US012590098B2

(12) United States Patent
Park et al.

(10) Patent No.: US 12,590,098 B2
(45) Date of Patent: Mar. 31, 2026

(54) PYRIMIDO PYRIMIDINONE COMPOUND AND PHARMACEUTICAL COMPOSITION COMPRISING THE SAME

(71) Applicant: AXCESO BIOPHARMA CO., LTD., Anyang-si (KR)

(72) Inventors: Young Jun Park, Yongin-si (KR); Sung Jun Park, Suwon-si (KR); Hyebin Yoo, Gwangju-si (KR); Hyunnam Song, Yongin-si (KR); Si-Eun Yun, Yongin-si (KR); Sojin Park, Yongin-si (KR); Joon Woo Kim, Yongin-si (KR); Sung Il Yoon, Hwaseong-si (KR)

(73) Assignee: AXCESO BIOPHARMA CO., LTD., Anyang-si (KR)

( * ) Notice: Subject to any disclaimer, the term of this patent is extended or adjusted under 35 U.S.C. 154(b) by 459 days.

(21) Appl. No.: 18/245,395

(22) PCT Filed: Sep. 15, 2021

(86) PCT No.: PCT/KR2021/012616

§ 371 (c)(1),
(2) Date: Mar. 15, 2023

(87) PCT Pub. No.: WO2022/060094

PCT Pub. Date: Mar. 24, 2022

(65) Prior Publication Data

US 2023/0348474 A1 Nov. 2, 2023

(30) Foreign Application Priority Data

Sep. 16, 2020 (KR) ........................ 10-2020-0119100

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC .................................................... C07D 487/04
See application file for complete search history.

(56) References Cited

FOREIGN PATENT DOCUMENTS

| | | | |
|---|---|---|---|
| KR | 10-0853975 | B1 | 8/2008 |
| KR | 10-2016-0040301 | A | 4/2016 |
| WO | 2005/011597 | A2 | 2/2005 |
| WO | 2006/024486 | A2 | 3/2006 |
| WO | 2018/009544 | A1 | 1/2018 |
| WO | 2019/204609 | A1 | 10/2019 |

OTHER PUBLICATIONS

Silverman, R. B., & Holladay, M. W. (2015). The Organic Chemistry of drug design and drug action (third edition). Academic Press. (Year: 2015).*

Cancer Risk and Prevention. American Cancer Society https://www.cancer.org/cancer/risk-prevention.html updated Jul. 15, 2025, accessed Jul. 24, 2025 (Year: 2025).*

Mary E Keir et al., "PD-1 and its Ligands in Tolerance and Immunity", Annu. Rev. Immunol, 2008, pp. 677-704, vol. 26.

Andrea Vannini et al., "αvβ3-integrin regulates PD-L1 expression and is involved in cancer immune evasion", Proc. Natl. Acad. Sci. U.S.A., Oct. 1, 2019, pp. 20141-20150, vol. 116, No. 40.

Rui-Yan Wu et al., Regorafenib Promotes Antitumor Immunity via Inhibiting PD-L1 and IDO1 Expression in Melanoma, Clinical Cancer Research, Jul. 15, 2019, pp. 4530-4541, vol. 25, No. 14.

Hanna Cho et al., "First SAR Study for Overriding NRAS Mutant Driven Acute Myeloid Leukemia", Journal of Medicinal Chemistry, 2018, pp. 8353-8373, vol. 61, No. 18.

International Search Report for PCT/KR2021/012616 dated Dec. 27, 2021.

European Patent Office, Communication issued Nov. 14, 2024 in copending Application No. 21 86 9716.

* cited by examiner

*Primary Examiner* — Andrew D Kosar
*Assistant Examiner* — Connor K English
(74) *Attorney, Agent, or Firm* — Sughrue Mion, PLLC

(57) ABSTRACT

Diclosed are a pyrimido pyrimidinone compound having an effect of inhibiting PD-L1 expression, a pharmaceutical composition containing the pyrimido pyrimidinone compound as an active ingredient, and uses of the compound or composition. The pyrimido pyrimidinone compound can be effectively used for the treatment or prevention of cancer.

9 Claims, 3 Drawing Sheets

【Fig. 1】
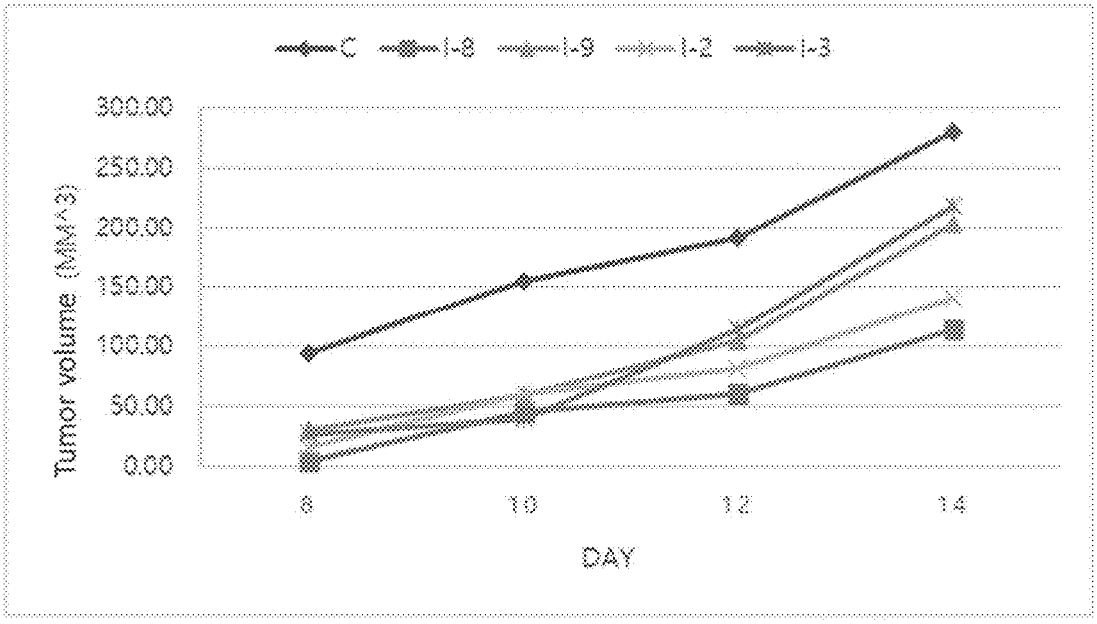
【Fig. 2】
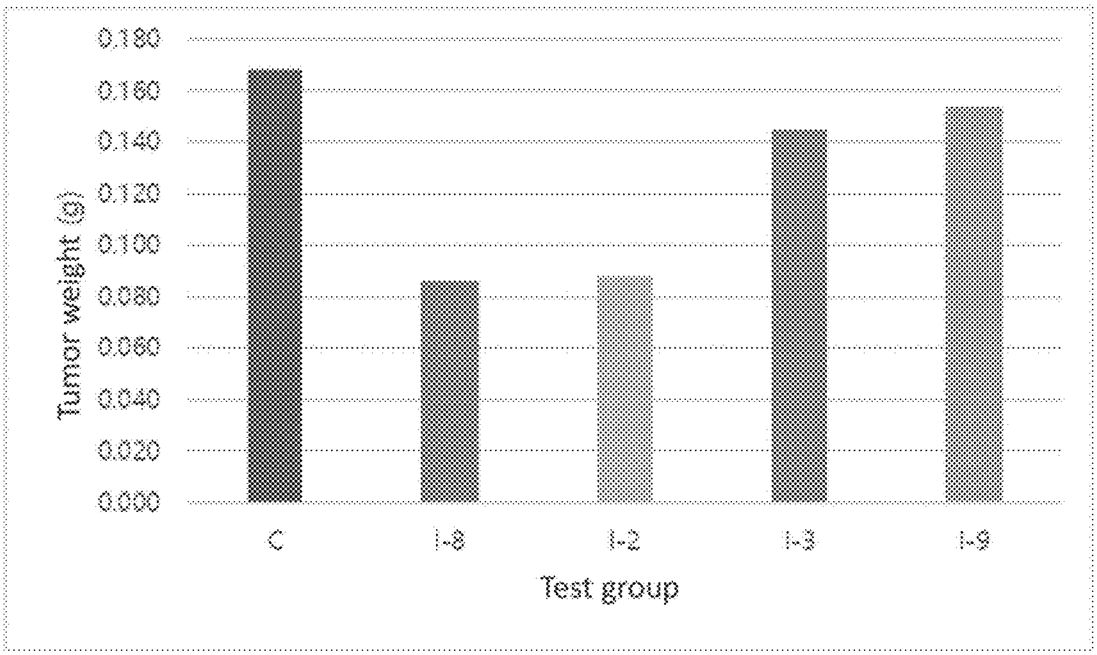

[Fig. 3]
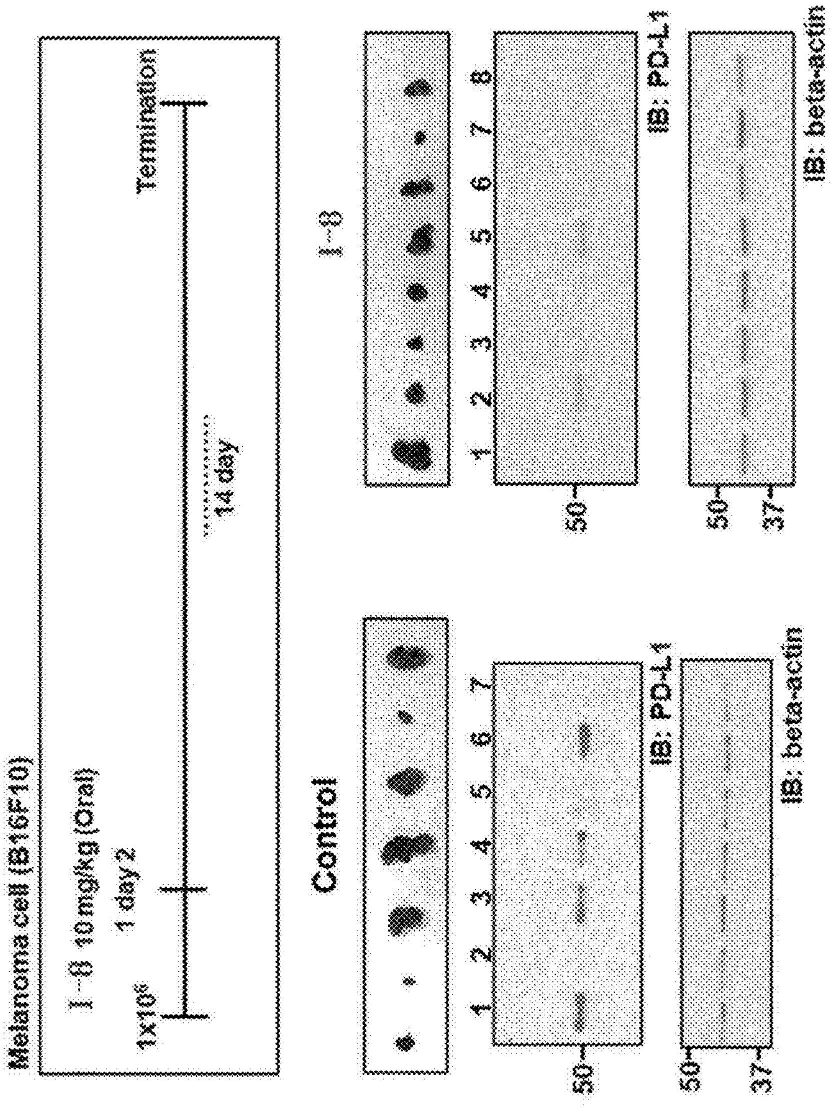

[Fig. 4]
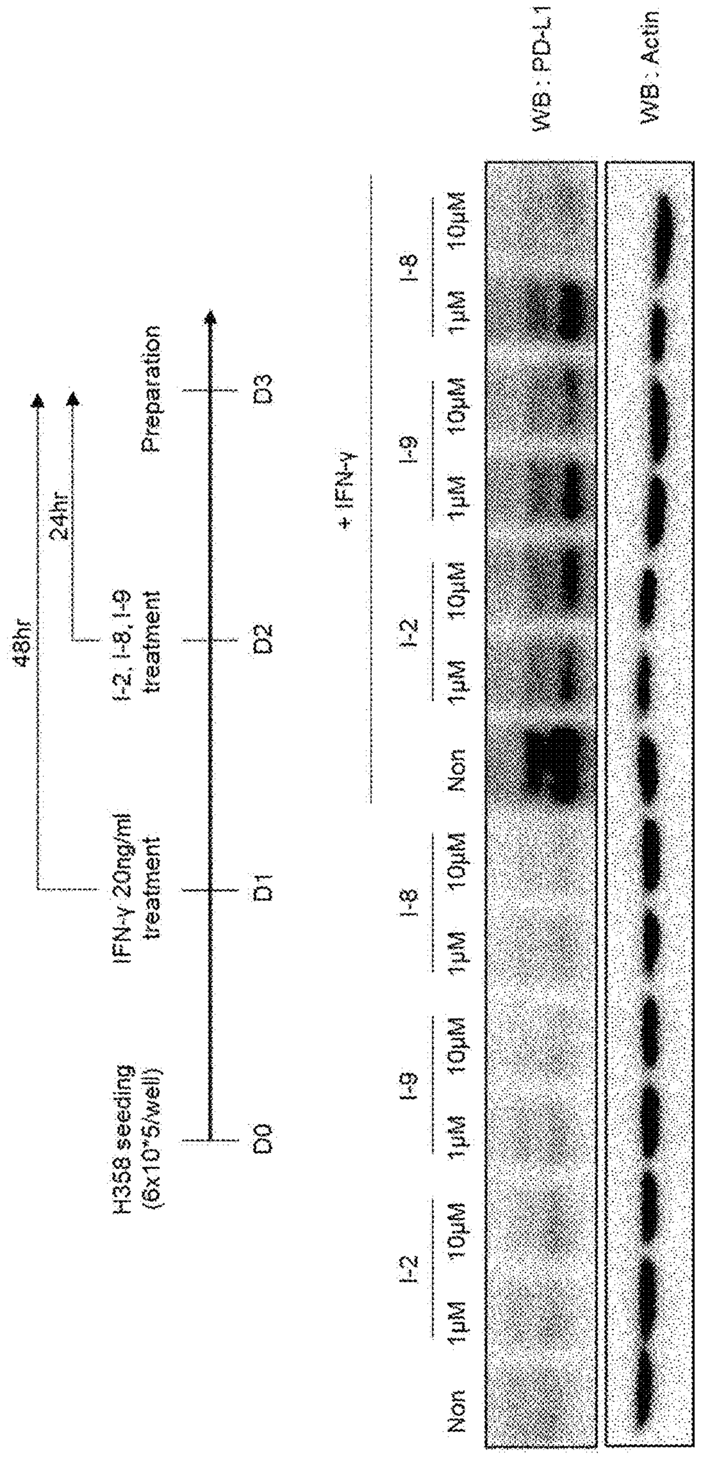

PYRIMIDO PYRIMIDINONE COMPOUND AND PHARMACEUTICAL COMPOSITION COMPRISING THE SAME

CROSS REFERENCE TO RELATED APPLICATIONS

This application is a National Stage of International Application No. PCT/KR2021/012616 filed Sep. 15, 2021, claiming priority based on Korean Patent Application No. 10-2020-0119100 filed Sep. 16, 2020.

TECHNICAL FIELD

The present invention relates to a pyrimido pyrimidinone compound and a pharmaceutical composition comprising the same, and more specifically to a pyrimido pyrimidinone compound having an effect of inhibiting PD-L1 expression and a pharmaceutical composition comprising the same as an active ingredient.

BACKGROUND ART

PD-1 (Programmed death-1, CD279) is a receptor protein on T cells, which is known to suppress activation signals from the T cell receptor when binding to its ligands PD-L1 (Programmed death-Ligand 1, CD274) or PD-L2 (Programmed death-Ligand 2, CD273). That is, when the PD-1 receptor protein of the T cells binds to the ligand PD-L1/2, the functional activity of the T-cells, including T-cell proliferation, cytokine secretion, and cytolytic activity, is reduced, thereby protecting normal cells. PD-1 and PD-L1/2 interaction downregulates the immune response in infections, tumors or autoimmune diseases (Keir Me, Butte M J, Freeman G J, et al. PD-1 and its ligands in tolerance and immunity. Annu. Rev. Immunol. 2008; 26).

Blockade of the PD-1/PD-L1 interaction using antibodies against PD-1 and PD-L1 has been shown to restore and enhance T cell activation in many systems. In cancer patients such as melanoma, non-small cell lung cancer, and renal cancer, PD-1/PD-L1 combination inhibitory therapy using a monoclonal antibody, and the like are known.

In a study on the regulation of PD-L1 expression and immune anticancer response in cancer cells by targeting αvβ3-integrin, it has been found that transplantation of β3-integrin-depleted tumor cells drastically reduces the growth of primary tumors, and the result is attributed to reduced PD-L1 expression. Thus, inhibition of β3-integrin can increase the efficacy of immune anticancer drugs against melanoma (Proc Natl Acad Sci USA., 2019 Oct. 1, 116(40), 20141-20150). It is known that retinoblastoma protein RB, known as a tumor suppressor, exhibits anticancer efficacy through inhibition of PD-L1 expression by inhibition of NF-kB activity. Also, in a melanoma model, curcumin and apigenin showed melanoma cell growth inhibitory effects, and in particular, apigenin was found to significantly suppress PD-L1 expression induced by IFN-γ. In addition, it is known that the expression of PD-L1 induced by IFN-γ is reduced by 40 to 80% in the lung cancer cell line A549 pretreated with EGCG and green tea extract (GTE). Meanwhile, in a kinase inhibitor library screening study that can increase immune anticancer effects against melanoma, regorafenib has been identified as the most powerful drug among about 20 drugs that reduced cell surface PD-L1 expression level by more than 50%. The drug strongly promotes anti-tumor efficacy when combined with IFN-γ or immune checkpoint blocker (ICB) in cells and in vivo, strongly suppresses JAK1/2-STAT1 and MAPK signaling and then reduces IFN-γ-induced PD-L1 and IDO1 expression (Clin Cancer Res., 2019 Jul. 15, 25(14), 4530-4541).

As protein kinase inhibitors, 3,4-dihydropyrimido[4,5-d]pyrimidin-2-one derivatives are known as Abl, BCR-Abl, Bmx, c-Raf, Csk, Fes, FGFR, Flt3, Ikk, IR , JNK, Lck, Mkk, PKC, PKD, Rsk, SAPK, Syk, Trk, RTK, Src, EGFR, IGF, Mek, Ros, Tie2 kinase activity inhibitors, but the effect of these derivatives on PD-L1 is not mentioned. It is also known that 3-phenyl-dihydropyrimido[4,5-d]pyrimidinone derivatives exhibit an inhibitory activity of 1 to 5 nM ($IC_{50}$) against Src kinase, but their effect on PD-L1 has not been mentioned either (International Patent Publication No. WO 2005/011597).

Therefore, there is a need for the development of compounds having PD-L1 expression inhibitory activity for anti-tumor efficacy.

DISCLOSURE

Technical Problem

An object of the present invention is to provide a compound of formula (I) exhibiting an effect of inhibiting PD-L1 expression or a pharmaceutically acceptable salt thereof.

Another object of the present invention is to provide a pharmaceutical composition comprising the compound of Formula (I) or a pharmaceutically acceptable salt thereof.

Technical Solution

One aspect of the present invention relates to a pyrimido pyrimidinone compound of the following formula (I) or a pharmaceutically acceptable salt thereof.

(I)

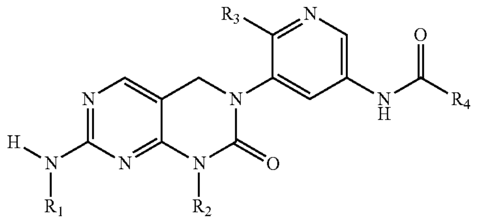

wherein, $R_1$ is a $C_5$-$C_{15}$ aryl, a $C_5$-$C_{15}$ heteroaryl, a $C_3$-$C_{10}$ cycloalkyl or a $C_3$-$C_{10}$ heterocycloalkyl;

$R_2$ is hydrogen, a $C_1$-$C_4$ alkyl or a $C_1$-$C_4$ alkoxy;

$R_3$ is hydrogen, halogen, a $C_1$-$C_4$ alkyl or a $C_1$-$C_4$ alkoxy; and $R_4$ is a $C_5$-$C_{15}$ aryl or a $C_5$-$C_{15}$ heteroaryl unsubstituted or substituted with a $C_1$-$C_4$ alkyl, a $C_1$-$C_4$ haloalkyl or a $C_5$-$C_{15}$ heteroaryl.

The term "$C_5$-$C_{15}$ aryl" as used herein includes both an aromatic group and a partially reduced derivative thereof. The aromatic group is a simple or fused ring type composed of 5 to 15 carbon atoms. Representative examples of the aryl include, but are not limited to, phenyl, naphthyl, tetrahydronaphthyl, and the like.

The term "$C_5$-$C_{15}$ heteroaryl" as used herein includes both a heteroaromatic group and a partially reduced derivative thereof. The heteroaromatic group is a simple or fused ring type composed of 5 to 15 carbon atoms, and contains one or more oxygen, sulfur or nitrogen. Representative examples of the heteroaryl include, but are not limited to, pyridinyl, furanyl, thiophenyl, indolyl, quinolinyl, imidazolinyl, oxazolyl, dihydrooxazolyl, thiazolyl, and the like.

The term "$C_3$-$C_{10}$ cycloalkyl" as used herein means a simple or fused cyclic hydrocarbon having 3 to 10 carbon atoms, and examples include, but are not limited to, cyclopropyl, cyclobutyl, cyclopentyl, cyclohexyl, and the like.

The term "$C_3$-$C_{10}$ heterocycloalkyl" as used herein means a functional group in which one or more of the ring carbon atoms of a simple or fused cyclic hydrocarbon having 3 to 10 carbon atoms is substituted with oxygen, sulfur or nitrogen, and examples include, but are not limited to, thiazolidinyl, oxiranyl, and the like.

The term "$C_1$-$C_4$ alkyl" as used herein means a straight or branched monovalent hydrocarbon having 1 to 4 carbon atoms, and examples include, but are not limited to, methyl, ethyl, n-propyl, i-propyl, n-butyl, i-butyl, t-butyl, and the like.

The term "$C_1$-$C_4$ alkoxy" as used herein means a straight or branched alkoxy group having 1 to 4 carbon atoms, and examples include, but are not limited to, methoxy, ethoxy, n-propanoxy, and the like.

The term "$C_1$-$C_4$ haloalkyl" as used herein means a straight or branched hydrocarbon having 1 to 4 carbon atoms substituted with one or more halogens selected from the group consisting of fluorine, chlorine, bromine and iodine, and examples include, but are not limited to, trifluoromethyl, trichloromethyl, trifluoroethyl, and the like.

In one embodiment of the present invention, the compound has formula (I)

wherein, $R_1$ is phenyl unsubstituted or substituted with halogen or hydroxyl;

$R_2$ is a $C_1$-$C_4$ alkyl;

$R_3$ is hydrogen, halogen, a $C_1$-$C_4$ alkyl or a $C_1$-$C_4$ alkoxy; and $R_4$ is phenyl unsubstituted or substituted with a $C_1$-$C_4$ alkyl, a $C_1$-$C_4$ haloalkyl or alkyldihydrooxazolyl, or alkylthiazolyl.

The term "alkyldihydrooxazolyl" as used herein means a dihydrooxazole group substituted with one or more $C_1$-$C_4$ alkyl groups, and examples include, but are not limited to, dimethyldihydrooxazolyl and the like.

The term "alkylthiazolyl" as used herein means a thiazolyl group substituted with one or more $C_1$-$C_4$ alkyl groups, and examples include, but are not limited to, t-butylthiazolyl and the like.

In one embodiment of the present invention, the compound has formula (I)

wherein, $R_1$ is phenyl, fluorophenyl or hydroxyphenyl;

$R_2$ is methyl;

$R_3$ is hydrogen, chloro, bromo, methyl or methoxy; and $R_4$ is trifluoromethylphenyl, t-butylphenyl, dimethyldihydrooxazolylphenyl or t-butylthiazolyl.

The pharmaceutically acceptable salt of the present invention may include both non-toxic inorganic and organic acid salts, and examples thereof include hydrochloride, phosphate, sulfate, nitrate, tartrate, methanesulfonate, p-toluenesulfonate, acetate, trifluoroacetate, citrate, maleate, succinate, oxalate, benzoate, fumarate, mandelate, propionate, lactate, glycolate, gluconate, galacturonate, glutamate, glutarate, glucuronate, aspartate, ascorbate, carbonate, vanillate, hydroiodide, malate, malonate, etc.

The representative compounds according to the present invention are selected from the following group.

N-(6-methyl-5-(1-methyl-2-oxo-7-(phenylamino)-1,2-dihydropyrimido[4,5-d]pyrimidin-3(4H)-yl)pyridin-3-yl)-3-(trifluoromethyl)benzamide (I-1);

3-(t-butyl)-N-(6-methyl-5-(1-methyl-2-oxo-7-(phenylamino)-1,2-dihydropyrimido[4,5-d]pyrimidin-3(4H)-yl) pyridin-3- yl)benzamide (I-2);

N-(6-methoxy-5-(1-methyl-2-oxo-7-(phenylamino)-1,2-dihydropyrimido[4,5-d]pyrimidin-3(4H)-yl)pyridin-3-yl)-3-(trifluoromethyl)benzamide (I-3);

4-(4,4-dimethyl-4,5-dihydrooxazol-2-yl)-N-(6-methyl-5-(1-methyl-2-oxo-7-(phenylamino)-1,2-dihydropyrimido[4,5-d]pyrimidin- 3(4H)-yl)pyridin-3-yl)benzamide (I-4);

3-(4,4-dimethyl-4,5-dihydrooxazol-2-yl)-N-(6-methyl-5-(1-methyl-2-oxo-7-(phenylamino)-1,2-dihydropyrimido[4,5-d]pyrimidin- 3(4H)-yl)pyridin-3-yl)benzamide (I-5);

3-(t-butyl)-N-(6-methoxy-5-(1-methyl-2-oxo-7-(phenylamino)-1,2-dihydropyrimido[4,5-d]pyrimidin-3(4H)-yl) pyridin-3- yl)benzamide (I-6);

3-(4,4-dimethyl-4,5-dihydrooxazol-2-yl)-N-(6-methoxy-5-(1-methyl-2-oxo-7-(phenylamino)-1,2-dihydropyrimido [4,5-d]pyrimidin- 3(4H)-yl)pyridin-3-yl)benzamide (I-7);

N-(6-chloro-5-(1-methyl-2-oxo-7-(phenylamino)-1,2-dihydropyrimido[4,5-d]pyrimidin-3(4H)-yl)pyridin-3-yl)-3-(trifluoromethyl)benzamide (I-8);

3-(t-butyl)-N-(6-chloro-5-(1-methyl-2-oxo-7-(phenylamino)-1,2-dihydropyrimido[4,5-d]pyrimidin-3(4H)-yl) pyridin-3- yl)benzamide (I-9);

2-(t-butyl)-N-(6-chloro-5-(1-methyl-2-oxo-7-(phenylamino)-1,2-dihydropyrimido[4,5-d]pyrimidin-3(4H)-yl) pyridin-3- yl)thiazole-4-carboxamide (I-10); and N-(6-chloro-5-(7-((4-hydroxyphenyl)amino)-1-methyl-2-oxo-1,2-dihydropyrimido[4,5-d]pyrimidin-3(4H)-yl)pyridin-3-yl)-3-trifluoromethyl)benzamide (I-11).

A process for preparing the compound of formula (I) according to the present invention is depicted in the following Reaction Scheme 1. However, one illustrated in the following Reaction Scheme represents only a typical process used in the present invention. The manipulation order, reagents, reaction conditions, etc. may be changed without limit.

[Reaction Scheme 1]

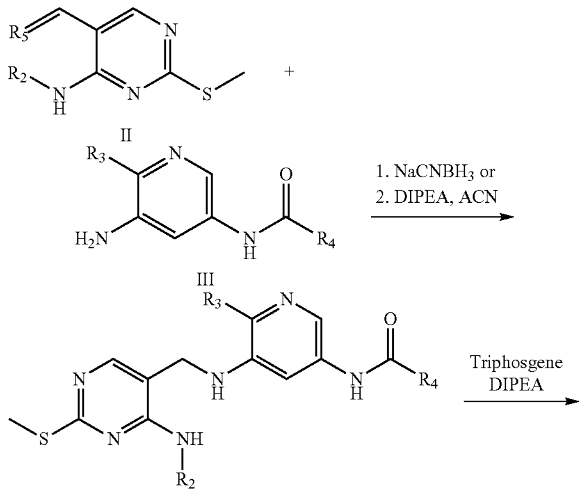

II

III

IV

-continued

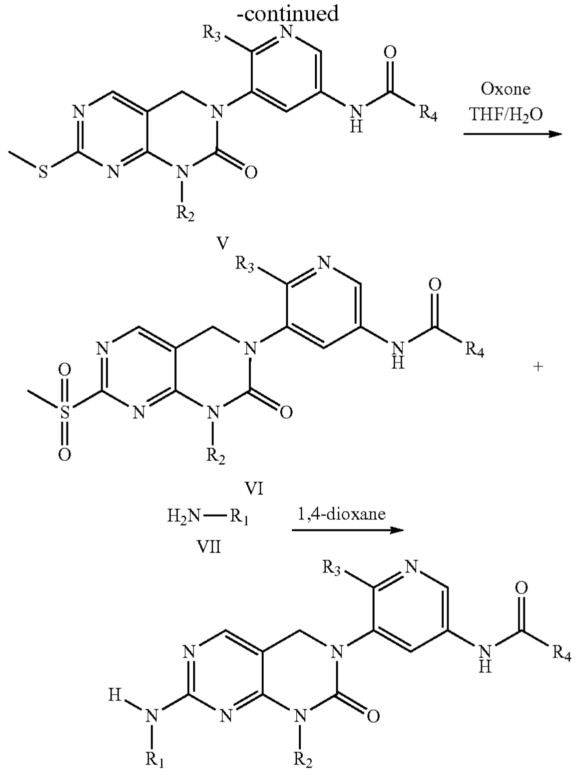

V

VI

VII

I

In Reaction Scheme 1, $R_1$, $R_2$, $R_3$ and $R_4$ are as defined in formula (I) above, and $R_5$ is halogen or oxo (═O).

In one embodiment of the present invention, $R_5$ is chloro, bromo, iodo or oxo (═O), in particular chloro or oxo (═O).

The Reaction Scheme 1 shows a process of four steps for preparing the compound of formula (I) using the compound of formula (II) and the compound of formula (III) as starting materials.

In step 1, the compound of formula (II) is reacted with the compound of formula (III) to give the compound of formula (IV).

At this time, when $R_5$ is halogen, an amination reaction is performed in the presence of an organic base to give the compound of formula (IV), and when $R_5$ is oxo (═O), a reducing agent is added to give the compound of formula (IV) by a reductive amination reaction. As the organic base, triethylamine, N,N-diisopropylethylamine (DIPEA), etc. may be used, and as the reducing agent, sodium borohydride ($NaBH_4$), sodium cyanoborohydride ($NaCNBH_3$), sodium triacetoxyborohydride ($Na(CH_3COO)_3BH$), and the like may be used.

As the reaction solvent, acetonitrile, tetrahydrofuran, 1,4-dioxane, chloroform, dichloromethane, 1,2-dichloroethane, dimethylformamide, dimethylacetamide, methyl alcohol, ethyl alcohol, etc. may be used, and the reaction temperature is preferably −10 to 25° C.

In step 2, triphosgene is added to the compound of formula (IV) for heterocyclic urea formation reaction to give the compound of Formula (V). In this case, the heterocyclic urea formation reaction may be performed in the presence of an organic base. As the organic base, triethylamine, N,N-diisopropylethylamine (DIPEA), etc. may be used.

As the reaction solvent, acetonitrile, tetrahydrofuran, 1,4-dioxane, etc. may be used, and the reaction temperature is preferably −10 to 100° C.

In step 3, the sulfide group of the compound of formula (V) is oxidized to give a sulfone compound of formula (VI) having a sulfone group.

The oxidation reaction may be performed using oxone, meta-chloroperoxybenzoic acid (mCPBA), or the like as an oxidizing agent.

As the reaction solvent, dichloromethane, 1,2-dichloroethane, acetonitrile, tetrahydrofuran, 1,4-dioxane, water, etc. may be used, and the reaction temperature is preferably −10 to 100° C.

In step 4, the compound of formula (I) is obtained by subjecting the compound of formula (VI) to a substitution reaction with an amine compound of formula (VII).

As the reaction solvent, acetonitrile, tetrahydrofuran, 1,4-dioxane, chloroform, dichloromethane, 1,2-dichloroethane, ethyl acetate, dimethylformamide, methyl alcohol, ethyl alcohol, etc. may be used. In the substitution reaction, an inorganic base or an organic base such as triethylamine, N,N-diisopropylethylamine, and pyridine may be used together, or an organic acid such as trifluoroacetic acid may be used together, if necessary. The reaction temperature is preferably 50 to 150° C., more preferably 80° C. to 100° C.

The compound of formula (II) and the compound of formula (III) may be prepared according to a known method or may be obtained as a commercially available product.

For example, processes for preparing the compound of formula (II) and the compound of formula (III) are depicted in the following Reaction Schemes 2 to 4, respectively. However, those illustrated in the following Reaction Schemes represent only typical processes used in the present invention. The manipulation order, reagents, reaction conditions, etc. may be changed without limit.

[Reaction Scheme 2]

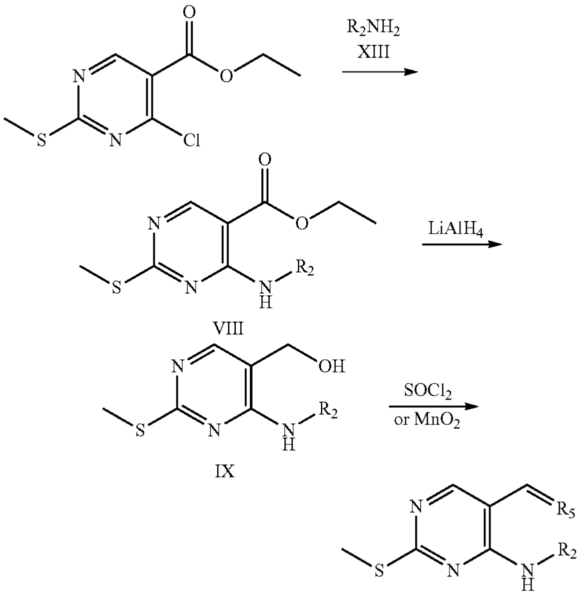

VIII

IX

II

In Reaction Scheme 2, $R_2$ is as defined in formula (I) above, and $R_5$ is as defined in Reaction Scheme 1 above.

As shown in Reaction Scheme 2, the compound of formula (II) may be prepared by reaction of ethyl 4-chloro-2-(methylthio)pyrimidine-5-carboxylate with an amine compound of formula (XIII) to give the compound of formula (VIII), a reduction reaction of the compound of formula (VIII) using a reducing agent such as lithium aluminum hydride ($LiAlH_4$) to give the compound of formula (IX), and halogenation of the alcohol group of the compound of formula (IX) using thionyl chloride ($SOCl_2$), etc. or aldehyde formation by oxidation using manganese dioxide ($MnO_2$), etc.

[Reaction Scheme 3]

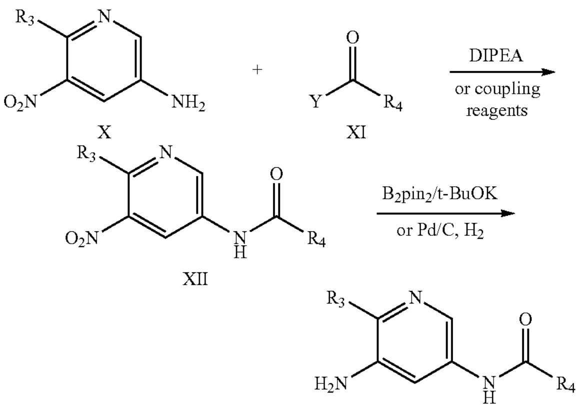

X XI XII III

In Reaction Scheme 3, $R_3$ and $R_4$ are as defined in formula (I) above, and Y is halogen or hydroxy.

In one embodiment of the invention, Y is chloro, bromo, iodo or hydroxy, in particular chloro or hydroxy.

As shown in Reaction Scheme 3, the compound of formula (III) may be prepared by reacting the compound of formula (X) and the compound of formula (XI) in the presence of an organic base such as DIPEA or a coupling agent to give the compound of formula (XII) and reducing the nitro group of the compound of formula (XII) to an amine group. In this case, the reduction reaction may be performed by using a combination of potassium t-butoxide and bis(pinacolato)diboron, or by using hydrogen gas on a palladium carbon catalyst.

[Reaction Scheme 4]

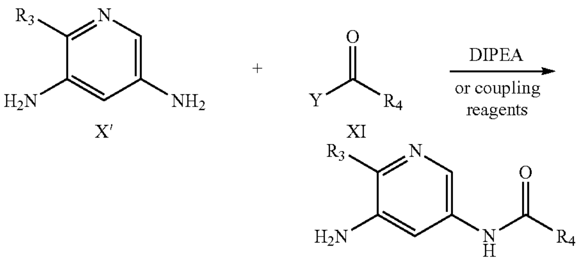

X' XI III

In Reaction Scheme 4, $R_3$ and $R_4$ are as defined in formula (I) above, and Y is as defined in Reaction Scheme 3 above.

Alternatively, the compound of formula (III) may be prepared by reacting a diamine pyridine compound of formula (X') with the compound of formula (XI) in the presence of an organic base such as DIPEA or a coupling agent, as shown in Reaction Scheme 4 above.

The compound of Formula I or a pharmaceutically acceptable salt thereof according to the present invention exhibits excellent PD-L1 expression inhibitory activity (Experimental Example 1).

One aspect of the present invention relates to a pharmaceutical composition for inhibiting programmed death-ligand 1 (PD-L1) comprising the compound of formula (I) or a pharmaceutically acceptable salt thereof together with a pharmaceutically acceptable carrier, in particular, a pharmaceutical composition for prevention or treatment of cancer.

In one embodiment of the present invention, the compound of formula (I) or pharmaceutically acceptable salt thereof induces anticancer effect through activation of immune cells by inhibiting the expression of PD-L1 and therefore can be effectively used for treating colon cancer, lung cancer, breast cancer, gastric cancer, cervical cancer, bladder cancer, blood cancer or non-Hodgkin's lymphoma.

The pharmaceutical composition according to the present invention can be administered orally, e.g., ingestion or inhalation; or parenterally, e.g., injection, deposition, implantation or suppositories. The injection can be, for example, intravenous, subcutaneous, intramuscular or intraperitoneal. Depending on the route of administration, the pharmaceutical composition of the present invention may be formulated as tablets, capsules, granules, fine subtilae, powders, sublingual tablets, suppositories, ointments, injection solutions, emulsions, suspensions, syrups, aerosols, etc. The above various forms of the pharmaceutical composition of the present invention can be prepared in a manner well known in the art using a pharmaceutically acceptable carrier(s) which are usually used for each form. Examples of the pharmaceutically acceptable carriers include excipient, binder, disintegrating agent, lubricant, preservative, antioxidant, isotonic agent, buffer, coating agent, sweetening agent, dissolvent, base, dispersing agent, wetting agent, suspending agent, stabilizer, colorant, etc.

The pharmaceutical composition according to the present invention contains 0.01 to 95 wt % of the compound of the present invention or pharmaceutically acceptable salt thereof depending on the form thereof.

The specific dosage of the present pharmaceutical composition can be varied with species of mammals including a human-being, body weight, gender, severity of disease, judgment of doctor, etc. It is preferable that 0.01 to 50 mg of the active ingredient is administered per kg of body weight a day for oral use, while 0.01 to 10 mg of the active ingredient is administered per kg of body weight a day for parenteral use. The total daily dosage can be administered once or over several times depending on the severity of disease, judgment of doctor, etc.

Advantageous Effects

The compound of the present invention can be used in a pharmaceutical composition for treating or preventing cancer, since it has an effect of inhibiting PD-L1 expression.

BRIEF DESCRIPTION OF FIGURES

FIG. 1 is a graph showing changes in tumor volumes over time after administration of example compounds to mice having cancer induced with B16F10 cells.

FIG. 2 is a graph showing weights of tumors excised from mice after administration of example compounds to mice having cancer induced with B16F10 cells.

FIG. 3 is a result of measuring the degree of suppression of PD-L1 expression through Western blotting in tumors excised from mice after administration of example compounds to mice having cancer induced with B16F10 cells.

FIG. 4 is a result of measuring the degree of suppression of PD-L1 expression through Western blotting after treatment of PD-L1 overexpressing cells with example compounds.

BEST MODE

The present invention is further illustrated by the following examples, which are not to be construed to limit the scope of the invention.

PREPARATION EXAMPLE 1

Preparation of the Compound of Formula (II)

Preparation Example 1-1: 5-(chloromethyl)-N-methyl-2-(methylthio)pyrimidin-4-amine (II-1)

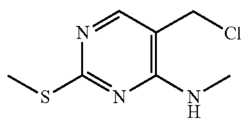

Ethyl 4-chloro-2-(methylthio)pyrimidine-5-carboxylate (10.00 g, 42.98 mmol) was dissolved in 100 mL of tetrahydrofuran, triethylamine (7.37 mL, 52.86 mmol) and 40% methylamine solution (3.54 g, 45.55 mmol) were added thereto, and the mixture was stirred at 20 to 25° C. for 16 hours. After the reaction was completed, the precipitated salt was filtered, the solvent was removed under reduced pressure, and the concentrated residue was extracted with saturated sodium bicarbonate solution and ethyl acetate. The organic layer was washed with brine, dried over anhydrous sodium sulfate, and concentrated under reduced pressure to give ethyl 4-(methylamino)-2-(methylthio)pyrimidine-5-carboxylate (VIII-1, 8.82 g, 90%).

$^1$H NMR (400 MHz, $CDCl_3$): δ 1.37 (t, 3H), 2.55 (s, 3H), 3.09 (d, 3H), 4.33 (q, 2H), 8.18 (bs, 1H), 8.61 (s, 1H)

Ethyl 4-(methylamino)-2-(methylthio)pyrimidine-5-carboxylate (VIII-1) (8.80 g, 38.72 mmol) obtained above was dissolved in 200 mL of anhydrous tetrahydrofuran and cooled to 0° C. 1M lithium aluminum hydride (116.16 mL, 116.16 mmol) was slowly added dropwise and stirred at 20 to 25° C. for 2 hours. When the reaction was completed, 5 mL of water, 15 mL of 15% sodium hydroxide solution, and 15 mL of water were slowly added dropwise to the reaction mixture in sequence, and then the reaction was terminated and stirred for 1 hour. After filtering the resulting white precipitate, the filtrate was extracted twice with ethyl acetate, and the organic layers were combined and extracted with brine. The organic layer was dried over anhydrous magnesium sulfate and concentrated under reduced pressure to give (4-(methylamino)-2-(methylthio)pyrimidin-5-yl) methanol (IX-1, 6.00 g, 84%).

$^1$H NMR (400 MHz, $CDCl_3$): δ 2.53 (s, 3H), 3.05 (d, 3H), 4.40 (s, 2H), 5.22 (m, 1H), 6.95 (br, 1H), 7.96 (s, 1H)

(4-(methylamino)-2-(methylthio)pyrimidin-5-yl)methanol (IX-1) (5.72 g, 30.88 mmol) obtained above was dissolved in 240 mL of anhydrous tetrahydrofuran and cool to 0° C. Then, thionyl chloride (5.59 mL, 77.19 mmol) was slowly added dropwise and stirred at 70° C. for 4 hours. The resulting white solid was filtered to give 7.20 g (100%) of the title compound.

Preparation Example 1-2: 4-(methylamino)-2-(methylthio)pyrimidine-5-carbaldehyde (II-2)

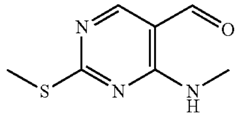

After adding 15 mL of dichloromethane to (4-(methylamino)-2-(methylthio)pyrimidin-5-yl)methanol (IX-1) (0.74 g, 4.00 mmol), manganese dioxide (3.47 g, 39.95 mmol) was added and stirred at 20 to 25° C. for 20 hours. After the reaction was completed, the reaction mixture was filtered through celite, and the solvent was removed under reduced pressure to give 0.67 g (92%) of the title compound.

$^1$H NMR (400 MHz, $CDCl_3$): δ 9.70 (s, 1H), 8.56 (bs, 1H), 8.30 (s, 1H), 3.12 (d, 3H), 2.57(s, 3H)

ES-MS m/z: 184.18 $[M+H]^+$

PREPARATION EXAMPLE 2

Preparation of the Compound of Formula (III)

Preparation Example 2-1: N-(5-amino-6-methylpyridin-3-yl)-3-(trifluoromethyl)benzamide (III-1)

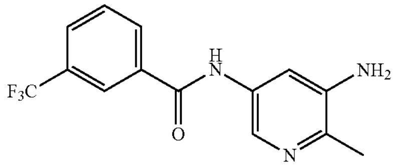 [SMILES: Cc1ncc(NC(=O)c2cccc(C(F)(F)F)c2)cc1N]

After dissolving 6-methyl-5-nitropyridin-3-amine (X-1) (1.00 g, 6.53 mmol) in 50 mL of dichloromethane, the mixture was cooled to 0° C. 3-(trifluoromethyl)benzoyl chloride (XI-1) (0.97 mL, 6.52 mmol) and N,N-diisopropylethylamine (3.33 mL, 19.59 mmol) were added to the reaction solution, and stirred at 20 to 25° C. for 1 hour. After the reaction was completed, extraction was performed sequentially using dichloromethane, distilled water and brine. The organic layer was dried over anhydrous sodium sulfate and concentrated under reduced pressure, and the concentrated residue was purified by column chromatography to give N-(6-methyl-5-nitropyridin-3-yl)-3-(trifluoromethyl)benzamide (XII-1) (1.76 g, 83%).

N-(6-methyl-5 -nitropyridin-3-yl)-3-(trifluoromethyl) benzamide (XII-1) (1.16 g, 3.57 mmol) obtained above was dissolved in 50 mL of methyl alcohol, 0.32 g of 10% palladium carbon was added and stirred for 3 hours under hydrogen atmosphere. After the reaction was completed, the reaction mixture was filtered through celite, washed with methanol, and then concentrated under reduced pressure to give 1.04 g (99%) of the title compound.

$^1$H NMR (400 MHz, $CDCl_3$): δ 2.55 (m, 3H), 4.07 (br, 2H), 6.71 (d, 1H), 7.01 (s, 1H), 7.29 (d, 1H), 7.45 (d, 1H), 7.65 (t, 1H), 7.85 (s, 1H), 8.02 (d, 1H)

Preparation Example 2-2: N-(5-amino-6-methylpyridin-3-yl)-3-(t-butyl)benzamide (III-2)

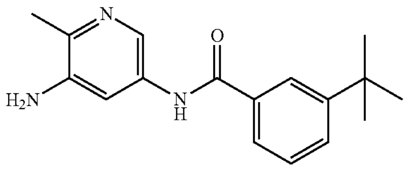 [SMILES: Cc1ncc(NC(=O)c2cccc(C(C)(C)C)c2)cc1N]

After suspending 3-(t-butyl)benzoic acid (0.6 g, 3.37 mmol) in 20 mL of dichloromethane, oxalyl chloride (0.58 mL, 6.73 mmol) and 1 to 2 drops of catalytic amount of dimethylformamide were added and stirred at room temperature for 3 hours. After the reaction was completed, the reaction solvent was evaporated under reduced pressure to give 3-(t-butyl)benzoyl chloride (XI-2) (0.67 g, Quant) without purification.

After dissolving 6-methyl-5-nitropyridin-3-amine (X-1) (0.90 g, 5.88 mmol) in 50 mL of dichloromethane, 3-(t-butyl)benzoyl chloride (XI-2) (1.15 g, 5.88 mmol) obtained above and N,N-diisopropylethylamine (3.07 mL, 17.63 mmol) were added and stirred at 20 to 25° C. for 1 hour. After the reaction was completed, extraction was performed sequentially using dichloromethane, distilled water and brine. The organic layer was dried over anhydrous sodium sulfate and concentrated under reduced pressure, and the concentrated residue was purified by column chromatography to give 3-(t-butyl)-N-(6-methyl-5-nitropyridin-3-yl) benzamide (XII-2) (1.39 g, 76%).

ES-MS m/z: 314.25 $[M+H]^+$ 3-(t-butyl)-N-(6-methyl-5-nitropyridin-3-yl)benzamide (XII-2) (1.39 g, 4.44 mmol) obtained above was dissolved in 40 mL of methyl alcohol, and 0.32 g of 10% palladium carbon was added and stirred for 3 hours under hydrogen atmosphere. After the reaction was completed, the reaction mixture was filtered through celite, washed with methanol, and then concentrated under reduced pressure to give the title compound (III-2) (1.18 g, 94%).

$^1$H NMR (400 MHz, $CDCl_3$): δ 1.34(s, 9H), 2.55 (m, 3H), 4.10 (br, 2H), 6.71 (s, 1H), 7.21 (d, 1H), 7.32 (d, 1H), 7.45 (d, 1H), 7.65 (t, 1H), 7.85 (s, 1H), 8.02 (d, 1H)

ES-MS m/z: 239.31 $[M+H]^+$

Preparation Example 2-3: N-(5-amino-6-methoxypyridin-3-yl)-3-(trifluoromethyl)benzamide (III-3)

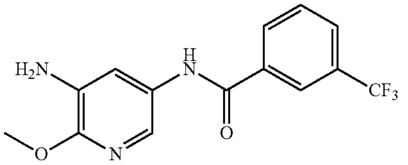 [SMILES: COc1ncc(NC(=O)c2cccc(C(F)(F)F)c2)cc1N]

After dissolving 2-methoxy-3,5-dinitropyridine (0.55 g, 2.76 mmol) in 20 mL of ethyl alcohol, 6N hydrochloric acid (4.00 mL) and iron (1.30 g) were added and refluxed for 1 hour. After the reaction was completed, the reaction mixture was cooled to 20 to 25° C., neutralized with 5M sodium hydroxide solution, and filtered through celite. The filtered solution was concentrated under reduced pressure, dissolved in ethyl acetate, extracted once with water, and washed with brine. The organic layer was dried over anhydrous sodium sulfate and concentrated under reduced pressure to give 2-methoxypyridine-3,5-diamine (X'-1) (0.21 g, 55%).

$^1$H NMR (400 MHz, $CDCl_3$): δ 3.23 (s, 3H), 3.90 (br, 4H), 6.46 (s, 1H), 6.69 (s, 1H)

ES-MS m/z: 140.11 $[M+H]^+$ 2-methoxypyridine-3,5-diamine (X'-1) (0.21 g, 1.51 mmol) obtained above was dissolved in 30 mL of acetone and cooled to 0° C., and triethylamine (0.23 g, 2.27 mmol) and 3-(trifluoromethyl)benzoyl chloride (XI-1) (0.25 g, 1.21 mmol) were added and stirred for 20 minutes. After the reaction was completed, the solvent was evaporated, and extraction was performed sequentially using ethyl acetate, distilled water, and brine. The organic layer was dried over anhydrous sodium sulfate, concentrated under reduced pressure, and purified by column chromatography to give 0.17 g (45%) of the title compound.

$^1$H NMR (400 MHz, $CDCl_3$): δ 3.23 (s, 3H), 3.90 (br, 2H), 6.59 (s, 1H), 6.78 (dd, 1H), 7.38 (d, 1H), 7.65 (t, 1H), 7.68 (s, 1H), 7.82 (d, 1H), 8.10 (s, 1H)

ES-MS m/z: 312.10 $[M+H]^+$

Preparation Example 2-4: N-(5-amino-6-methylpyridin-3-yl)-4-(4,4-dimethyl-4,5-dihydrooxazol-2-yl)benzamide (III -4)

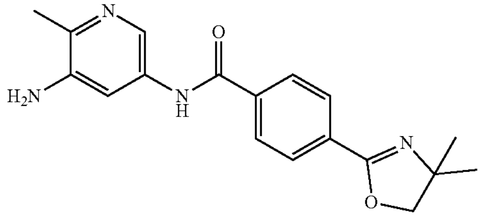

6-methyl-5-nitropyridin-3-amine (X-1) (1.00 g, 6.52 mmol) was dissolved in 50 mL of dichloromethane and cooled to 0° C., and N, N-diisopropylethylamine (3.41 mL, 19.59 mmol) and 4-(4,4-dimethyl-4,5-dihydrooxazol-2-yl) benzoyl chloride (XI-3) (1.55 g, 6.52 mmol) were added and stirred for 2 hours. After the reaction was completed, extraction was sequentially performed using dichloromethane, distilled water and brine. The organic layer was dried over anhydrous sodium sulfate and concentrated under reduced pressure, and the concentrated residue was purified by column chromatography to give 4-(4,4-dimethyl-4,5-dihydrooxazol-2-yl)-N-(6-methyl-5-nitropyridin-3-yl)benzamide (XII-6) (1.99 g, 86%).

ES-MS m/z: 355.25 $[M+H]^+$ 4-(4,4-dimethyl-4,5-dihydrooxazol-2-yl)-N-(6-methyl-5-nitropyridin-3-yl)benzamide (XII-6) (1.95 g, 5.50 mmol) obtained above was dissolved in 50 mL of methyl alcohol, and 0.30 g of 10% palladium carbon was added and stirred for 5 hours under hydrogen atmosphere. Then, 1.64 g (92%) of the title compound was obtained in the same manner as in Preparation Example 2-1.

ES-MS m/z: 325.25 $[M+H]^+$

Preparation Example 2-5: N-(5-amino-6-methylpyridin-3-yl)-3-(4,4-dimethyl-4,5-dihydrooxazol-2-yl)benzamide (III-5)

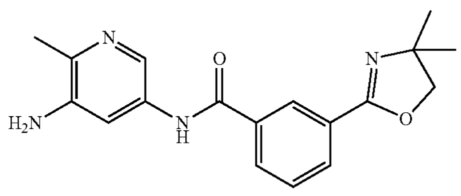

6-methyl-5-nitropyridin-3-amine (X-1) (1.00 g, 6.52 mmol) was dissolved in 60 mL of tetrahydrofuran and cooled to 0° C., and N,N-diisopropylethylamine (3.41 mL, 19.59 mmol) and 3-(4,4-dimethyl-4,5-dihydrooxazol-2-yl) benzoyl chloride (XI-4) (1.55 g, 6.52 mmol) were added and stirred for 2 hours. After the reaction was completed, extraction was sequentially performed using dichloromethane, distilled water and brine. The organic layer was dried over anhydrous sodium sulfate and concentrated under reduced pressure, and the concentrated residue was purified by column chromatography to give 3-(4,4-dimethyl-4,5-dihydrooxazol-2-yl)-N-(6-methyl-5-nitropyridin-3-yl)benzamide (XII-7) (1.39 g, 60%).

3-(4,4-dimethyl-4,5 -dihydrooxazol-2-yl)-N-(6-methyl-5-nitropyridin-3-yl)benzamide (XII-7) (1.39 g, 3.92 mmol) obtained above was dissolved in 30 mL of methyl alcohol, 0.30 g of 10% palladium carbon was added and stirred for 3 hours under hydrogen atmosphere. Then, 1.17 g (92%) of the title compound was obtained in the same manner as in Preparation Example 2-1.

ES-MS m/z: 325.16 $[M+H]^+$

Preparation Example 2-6: N-(5-amino-6-methoxypyridin-3-yl)-3-(t-butyl)benzamide (III-6)

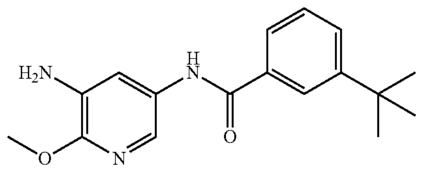 [SMILES: COc1ncc(NC(=O)c2cccc(C(C)(C)C)c2)cc1N]

After dissolving 2-methoxypyridine-3,5-diamine (X'-1) (0.44 g, 3.18 mmol) in 40 mL of acetone and cooling to 0° C., triethylamine (0.48 g, 4.77 mmol) and 3-(t-butyl)benzoyl chloride (XI-2) (0.50 g, 2.54 mmol) were added and stirred for 2 hours. After the reaction was completed, the solvent was evaporated and extraction was sequentially performed using ethyl acetate, distilled water, and brine. The organic layer was dried over anhydrous sodium sulfate and concentrated under reduced pressure to give 0.34 g (45%) of the title compound.

ES-MS m/z: 300.28 $[M+H]^+$

Preparation Example 2-7: N-(5-amino-6-methoxypyridin-3-yl)-3-(4,4-dimethyl-4,5-dihydrooxazol-2-yl)benzamide (III-7)

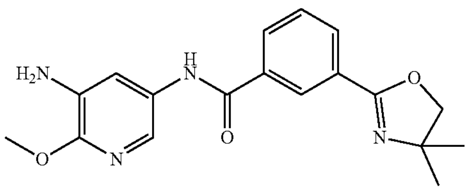

After dissolving 2-methoxypyridine-3,5-diamine (X'-1) (0.40 g, 2.87 mmol) in 40 mL of acetone and cooling to 0° C., triethylamine (0.44 g, 4.31 mmol) and 3-(4,4-dimethyl-4,5-dihydrooxazol-2-yl)benzoyl chloride (XI-4) (0.55 g, 2.30 mmol) were added and stirred for 2 hours. After the reaction was completed, the solvent was evaporated and extraction was sequentially performed using ethyl acetate, distilled water, and brine. The organic layer was dried over anhydrous sodium sulfate and concentrated under reduced pressure to give 0.34 g (43%) of the title compound.

ES-MS m/z: 341.36 $[M+H]^+$

Preparation Example 2-8: N-(5-amino-6-chloropyridin-3-yl)-3-(trifluoromethyl)benzamide Trifluoroacetate (III-8)

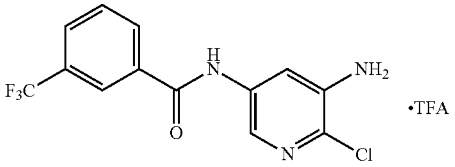 [SMILES: Nc1cc(NC(=O)c2cccc(C(F)(F)F)c2)cnc1Cl]

After dissolving t-butyl (5-amino-2-chloropyridin-3-yl) carbamate (1.20 g, 4.92 mmol) in 60 mL of dichloromethane and cooling to 0° C., N,N-diisopropylethylamine (2.51 mL, 14.77 mmol) and 3-(trifluoromethyl)benzoyl chloride (XI-1) (1.13 g, 5.42 mmol) were added and stirred at 20 to 25° C. for 4 hours. After the reaction was completed, extraction was sequentially performed using dichloromethane, distilled water, and saturated sodium chloride solution. The organic layer was dried over anhydrous sodium sulfate and concentrated under reduced pressure, and the residue was purified by column chromatography to give 1.59 g of t-butyl (2-chloro-5-(3-(trifluoromethyl)benzamido)pyridin-3-ylcarbamate (78%).

$^1H$ NMR (400 MHz, $CDCl_3$): δ 1.53 (s, 9H), 7.06 (br, 1H), 7.64 (m, 1H), 7.84 (m, 1H), 8.10 (m, 3H), 8.58 (d, 1H), 8.78 (d, 1H).

1.50 g (3.61 mmol) of t-butyl (2-chloro-5-(3-(trifluoromethyl)benzamido)pyridin-3-ylcarbamate obtained above was dissolved in dichloromethane:trifluoroacetic acid (1:1) and stirred at 20 to 25° C. for 5 hours. After the reaction was completed, the reaction solvent was evaporated under reduced pressure to give 1.10 g (71%) of the title compound trifluoroacetate.

$^1H$ NMR (400 MHz, DMSO-$d_6$): δ 5.69 (br, 2H), 5.76 (br, 1H), 7.73 (d, 1H), 7.79 (t, 1H), 7.97 (m, 2H), 8.26 (m, 2H), 10.53 (S, 1H).

Preparation Example 2-9: N-(5-amino-6-chloropyridin-3-yl)-3-(t-butyl)benzamide Trifluoroacetate (III-9)

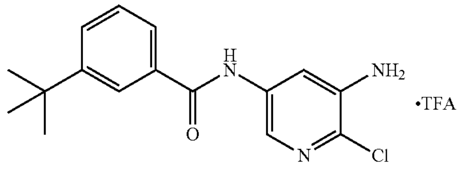 [SMILES: CC(C)(C)c1cccc(C(=O)Nc2cnc(Cl)c(N)c2)c1]

After dissolving t-butyl (5-amino-2-chloropyridin-3-yl) carbamate (0.84 g, 3.45 mmol) in 50 mL of dichloromethane and cooling to 0° C., N,N-diisopropylethylamine (1.76 mL, 10.34 mmol) and 3-(t-butyl)benzoyl chloride (XI-2) (0.68 g, 3.45 mmol) were added and stirred at 20 to 25° C. for 5 hours. Then, t-butyl (5-(3-(t-butyl)benzamido)-2-chloropyridin-3-yl)carbamate (0.90 g, 65%) was obtained in the same manner as in Preparation Example 2-8.

After dissolving t-butyl (5-(3-(t-butyl)benzamido)-2-chloropyridin-3-yl)carbamate (0.88 g, 2.18 mmol) obtained above in dichloromethane:trifluoroacetic acid (1:1), 0.88 g of the title compound trifluoroacetate was quantitatively obtained in the same manner as in Preparation Example 2-8.

$^1$H NMR (400 MHz, DMSO-$d_6$): δ 1.38 (s, 9H), 5.69 (br, 2H), 5.76 (br, 1H), 7.73 (d, 1H), 7.79 (t, 1H), 7.97 (m, 2H), 8.26 (m, 2H), 10.53 (S, 1H).

Preparation Example 2-10: N-(5-amino-6-chloropyridin-3-yl)-2-(t-butyl)thiazole-4-carboxamide Trifluoroacetate (III-10)

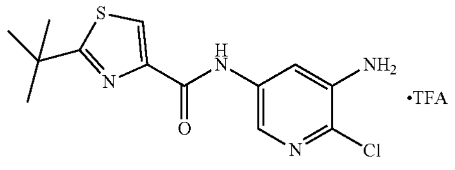 [SMILES: CC(C)(C)c1nc(C(=O)Nc2cnc(Cl)c(N)c2)cs1]

After dissolving t-butyl (5-amino-2-chloropyridin-3-yl) carbamate (0.84 g, 3.45 mmol) in 50 mL of dichloromethane and cooling to 0° C., N,N-diisopropylethylamine (1.76 mL, 10.34 mmol) and 2-(t-butyl)thiazole-4-carbonyl chloride (XI-5) (0.70 g, 3.45 mmol) were added and stirred at 20 to 25° C. for 5 hours. In the same manner as in Preparation Example 2-8, t-butyl (5-(2-(t-butyl)thiazole-4-carboxamido)-2-chloropyridin-3-yl)carbamate (0.94 g, 67%) was obtained.

After dissolving t-butyl (5-(2-(t-butyl)thiazole-4-carboxamido)-2-chloropyridin-3-yl)carbamate (0.92 g, 2.24 mmol) obtained above in dichloromethane:trifluoroacetic acid (1:1), 0.92 g of the title compound trifluoroacetate was quantitatively obtained in the same manner as in Preparation Example 2-8.

PREPARATION EXAMPLE 3

Preparation of the Compound of Formula (IV)

Preparation Example 3-1: N-(6-methyl-5-(((4-(methylamino)-2-(methylthio)pyrimidin-5-yl)methyl)amino)pyridin-3-yl)-3-(trifluoromethyl)benzamide (IV-1)

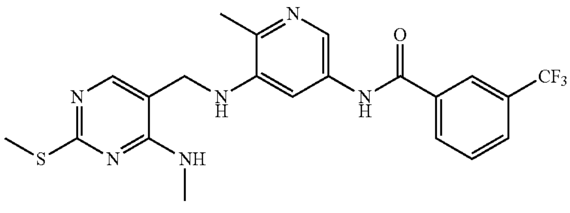 [SMILES: CNc1nc(SC)ncc1CNc1cc(NC(=O)c2cccc(C(F)(F)F)c2)cnc1C]

After dissolving the compound (III-1) (0.60 g 2.03 mmol) prepared in Preparation Example 2-1 in 50 mL of acetonitrile, N,N-diisopropylethylamine (1.06 mL, 6.10 mmol) was added at 0° C. The compound (II-1) (0.40 g, 1.63 mmol) prepared in Preparation Example 1-1 was dissolved in 30 mL of acetonitrile and slowly added dropwise to the reaction solution, followed by stirring at 20 to 25° C. for 1 hour. The reaction solvent was evaporated under reduced pressure and extraction was sequentially performed using ethyl acetate, water and brine. The organic layer was dried over anhydrous sodium sulfate and concentrated under reduced pressure. The concentrated residue was purified by column chromatography to give 0.70 g (70%) of the title compound.

$^1$H NMR (400 MHz, $CDCl_3$): δ 2.55 (s, 3H), 3.05 (d, 3H), 4.16 (s, 2H), 5.57 (m, 1H), 6.88 (dd, 1H), 7.29 (d, 1H), 7.43 (d, 1H), 7.65 (t, 1H), 7.82-7.85 (m, 2H), 7.93 (s, 1H), 8.06 (d, 1H), 8.12 (s, 1H)

ES-MS m/z: 463.03 $[M+H]^+$

Preparation Example 3-2: 3-(t-butyl)-N-(6-methyl-5-(((4-(methylamino)-2-(methylthio)pyrimidin-5-yl)methyl)amino)pyridin-3-yl)benzamide (IV-2)

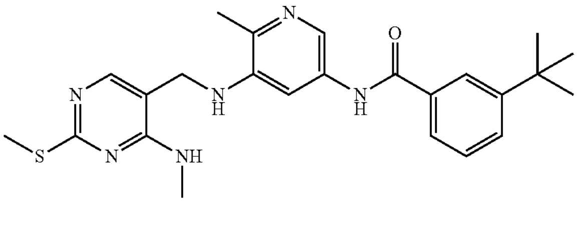 [SMILES: CNc1nc(SC)ncc1CNc1cc(NC(=O)c2cccc(C(C)(C)C)c2)cnc1C]

The compound (III-2) (0.90 g, 3.18 mmol) prepared in Preparation Example 2-2 instead of the compound (III-1) and the compound (II-1) (0.76 g, 3.16 mmol) prepared in Preparation Example 1-1 were used to give 0.80 g (56%) of the title compound in the same manner as in Preparation Example 3-1.

$^1$H NMR (400 MHz, $CDCl_3$): 61.34 (s, 9H), 2.47 (s, 6H), 2.55 (s, 3H), 4.16 (s, 2H), 4.32 (m, 2H), 6.76 (dd, 1H), 7.36 (m, 1H), 7.54 (m, 1H), 7.75 (m, 2H), 7.98 (m, 1H), 8.25 (m, 1H)

ES-MS m/z: 451.14 $[M+H]^+$

Preparation Example 3-3: 3-(t-butyl)-N-(6-methyl-5-(((4-(methylamino)-2-(methylthio)pyrimidin-5-yl)methyl)amino)pyridin-3-yl)benzamide (IV-2)

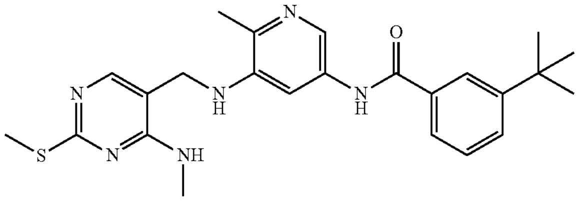 [SMILES: CNc1nc(SC)ncc1CNc1cc(NC(=O)c2cccc(C(C)(C)C)c2)cnc1C]

Instead of the compound (III-1), the compound (III-2) (2.08 g, 7.33 mmol) prepared in Preparation Example 2-2 was dissolved in 50 mL of methyl alcohol, and acetic acid (0.88 mL, 15.28 mmol) and the compound (II-2) (1.12 g, 6.11 mmol) prepared in Preparation Example 1-2 were added and stirred for 15 minutes. After adding sodium cyanoborohydride (2.30 g, 36.68 mmol) to the reaction solution, the temperature was raised to 45° C. and stirred for 18 hours. After the reaction was completed, the mixture was cooled to 20 to 25° C., the reaction solvent was evaporated under reduced pressure, and extraction was performed using ethyl acetate and saturated sodium hydrogen carbonate solution. The organic layer was dried over anhydrous sodium sulfate and concentrated under reduced pressure. The concentrated residue was purified by column chromatography to give 1.10 g (40%) of the title compound.

ES-MS m/z: 451.14 $[M+H]^+$

Preparation Example 3-4: N-(4-methoxy-3-(((4-(methylamino)-2-(methylthio)pyrimidin-5-yl)methyl)amino)pyridin-3-yl)-3-(trifluoromethyl)benzamide (IV-3)

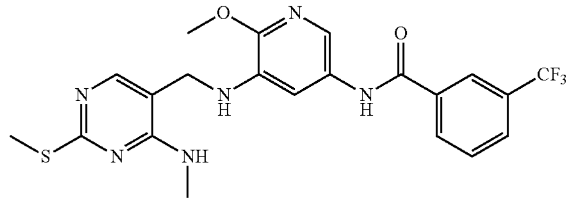 [SMILES: CNc1nc(SC)ncc1CNc1cc(NC(=O)c2cccc(C(F)(F)F)c2)cnc1OC]

0.10 g (30%) of the title compound was obtained in the same manner as in Preparation Example 3-1 using the compound (III-3) (0.17 g, 0.69 mmol) prepared in Preparation Example 2-3 instead of the compound (III-1).

$^1$H NMR (400 MHz, $CDCl_3$): δ 2.55 (s, 3H), 2.87 (d, 3H), 4.01 (s, 3H), 4.25 (s, 2H), 5.60 (dd, 2H), 6.88 (dd, 1H), 7.12 (d, 1H), 7.42-7.89 (m, 4H), 7.93 (s, 1H), 8.12 (s, 1H)

ES-MS m/z: 527.97 $[M+H]^+$

Preparation Example 3-5: 4-(4,4-dimethyl-4,5-dihydrooxazol-2-yl)-N-(6-methyl-5-(((4-(methylamino)-2-(methylthio)pyrimidin-5-yl)methyl)amino)pyridin-3-yl)benzamide (IV-4)

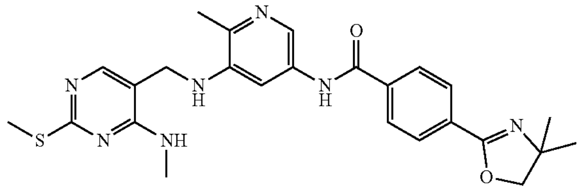

0.45 g (30%) of the title compound was obtained in the same manner as in Preparation Example 3-1 using the compound (III-4) (1.00 g, 3.08 mmol) prepared in Preparation Example 2-4 instead of the compound (III-1).

ES-MS m/z: 492.54 $[M+H]^+$

Preparation Example 3-6: 3-(4,4-dimethyl-4,5-dihydrooxazol-2-yl)-N-(6-methyl-5-(((4-(methylamino)-2-(methylthio)pyrimidin-5-yl)methyl)amino)pyridin-3-yl)benzamide (IV-5)

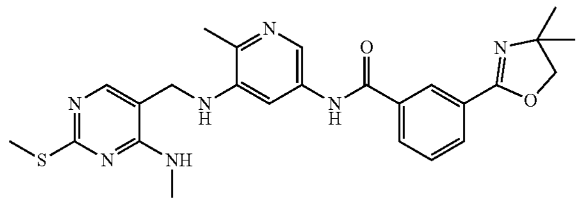

0.40 g (30%) of the title compound was obtained in the same manner as in Preparation Example 3-1 using the compound (III-5) (1.00 g, 3.08 mmol) prepared in Preparation Example 2-5 instead of the compound (III-1).

ES-MS m/z: 492.54 $[M+H]^+$

Preparation Example 3-7: 3-(t-butyl)-N-(6-methoxy-5-(((4-(methylamino)-2-(methylthio)pyrimidin-5-yl)methyl)amino)pyridin-3-yl)benzamide (IV-6)

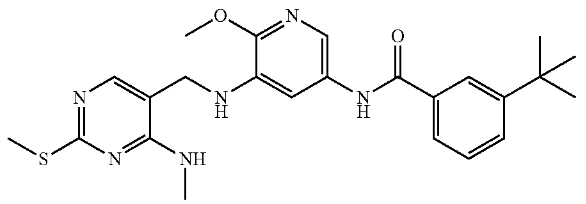 [SMILES: CNc1nc(SC)ncc1CNc1cc(NC(=O)c2cccc(C(C)(C)C)c2)cnc1OC]

0.18 g (51%) of the title compound was obtained in the same manner as in Preparation Example 3-1 using the compound (III-6) (0.34 g, 1.14 mmol) prepared in Preparation Example 2-6 instead of the compound (III-1).

ES-MS m/z: 467.61 $[M+H]^+$

Preparation Example 3-8: 3-(4,4-dimethyl-4,5-dihydrooxazol-2-yl)-N-(6-methoxy-5-(((4-(methylamino)-2-(methylthio)pyrimidin-5-yl)methyl)amino)pyridin-3-yl)benzamide (IV-7)

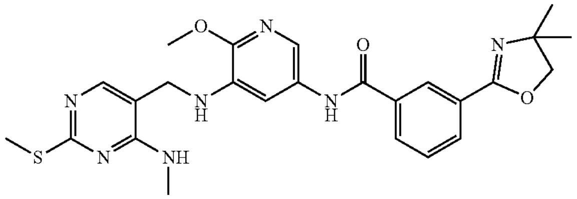

0.15 g (45%) of the title compound was obtained in the same manner as in Preparation Example 3-1 using the compound (III-7) (0.34 g, 1.00 mmol) prepared in Preparation Example 2-7 instead of the compound (III-1).

ES-MS m/z: 508.55 $[M+H]^+$

Preparation Example 3-9: N-(6-chloro-5-(((4-(methylamino)-2-(methylthio)pyrimidin-5-yl)methyl)amino)pyridin-3-yl)-3-(trifluoromethyl)benzamide (IV-8)

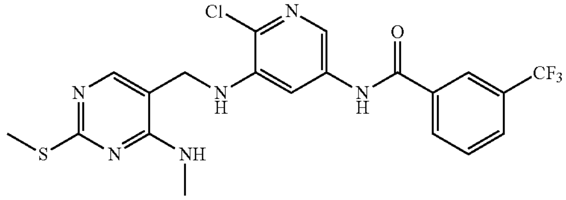 [SMILES: CNc1nc(SC)ncc1CNc1cc(NC(=O)c2cccc(C(F)(F)F)c2)cnc1Cl]

0.26 g (41%) of the title compound was obtained in the same manner as in Preparation Example 3-1 using the compound (III-8) (1.15 g 1.99 mmol) prepared in Preparation Example 2-8 instead of the compound (III-1).

Preparation Example 3-10: 3-(t-butyl)-N-(6-chloro-5-(((4-(methylamino)-2-(methylthio)pyrimidin-5-yl)methyl)amino)pyridin-3-yl)benzamide (IV-9)

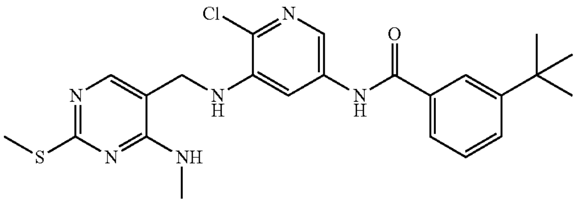 [SMILES: CNc1nc(SC)ncc1CNc1cc(NC(=O)c2cccc(C(C)(C)C)c2)cnc1Cl]

0.28 g (41%) of the title compound was obtained in the same manner as in Preparation Example 3-1 using the compound (III-9) (1.17 g 2.91 mmol) prepared in Preparation Example 2-9 instead of the compound (III-1).

Preparation Example 3-11: 2-(t-butyl)-N-(6-chloro-5-(((4-(methylamino)-2-(methylthio)pyrimidin-5-yl)methyl)amino)pyridin-3-yl)thiazole-4-carboxamide (IV-10)

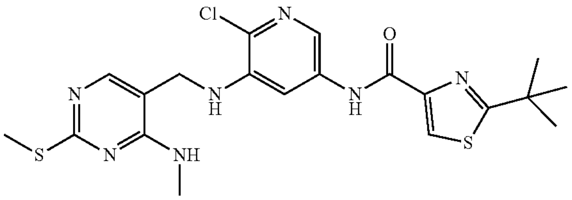 [SMILES: CNc1nc(SC)ncc1CNc1cc(NC(=O)c2csc(C(C)(C)C)n2)cnc1Cl]

0.32 g (41%) of the title compound was obtained in the same manner as in Preparation Example 3-1 using the compound (III-10) (0.67 g 3.33 mmol) prepared in Preparation Example 2-10 instead of the compound (III-1).

$^1$H NMR (400 MHz, $CDCl_3$): δ 9.24 (s, 1H), 8.07 (m, 1H), 7.95 (s, 1H), 7.87 (d, 1H), 5.45 (br, 1H), 4.15-4.19 (m, 2H), 3.07 (d, 2H), 2.55 (s, 3H), 1.47 (s, 9H).

PREPARATION EXAMPLE 4

Preparation of the Compound of Formula (V)

Preparation Example 4-1: N-(6-methyl-5-(1-methyl-7-(methylthio)-2-oxo-1,2-dihydropyrimido[4,5-d]pyrimidin-3(4H)-yl)pyridin-3-yl)-3- (trifluoromethyl)benzamide (V-1)

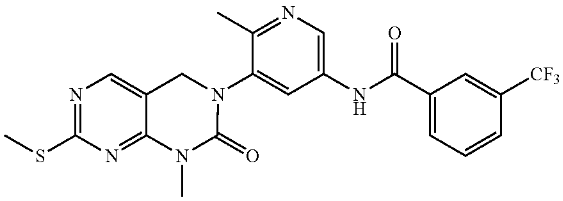 [SMILES: CSc1ncc2c(n1)N(C)C(=O)N(c1cc(NC(=O)c3cccc(C(F)(F)F)c3)cnc1C)C2]

After dissolving the compound (IV-1) (0.70 g, 1.51 mmol) prepared in Preparation Example 3-1 in 60 mL of 1,4-dioxane, N,N-diisopropylethylamine (0.78 mL, 4.54 mmol) and triphosgene (0.63 g, 2.12 mmol) were added at 0° C. and stirred at 100° C. for 3 hours. After the reaction was completed, extraction was performed with saturated sodium hydrogen carbonate solution and ethyl acetate, and the organic layer was washed with brine. The organic layer was dried over anhydrous sodium sulfate and concentrated under reduced pressure, and the concentrated residue was purified by column chromatography to give 0.37 g (50%) of the title compound.

$^1$H NMR (400 MHz, $CDCl_3$): δ 2.55 (s, 3H), 2.63 (s, 3H), 3.65 (d, 3H), 5.16 (s, 2H), 6.88 (dd, 1H), 7.29 (d, 1H), 7.43 (d, 1H), 7.65 (t, 1H), 7.82-7.85 (m, 2H), 7.93 (s, 1H), 8.12 (s, 1H)

ES-MS m/z: 489.50 $[M+H]^+$

Preparation Example 4-2: 3-(t-butyl)-N-(6-methyl-5-(1-methyl-7-(methylthio)-2-oxo-1,2-dihydropyrimido[4,5-d]pyrimidin-3(4H)-yl)pyridin-3-yl)benzamide (V-2)

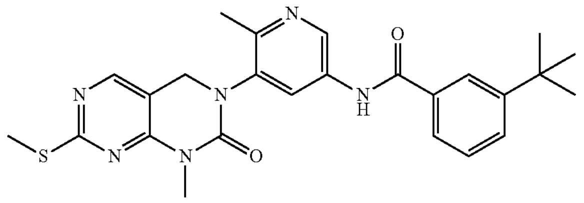 [SMILES: CSc1ncc2c(n1)N(C)C(=O)N(c1cc(NC(=O)c3cccc(C(C)(C)C)c3)cnc1C)C2]

0.50 g (60%) of the title compound was obtained in the same manner as in Preparation Example 4-1 using the compound (IV-2) (0.80 g, 1.78 mmol) prepared in Preparation Example 3-2 instead of the compound (IV-1).

$^1$H NMR (400 MHz, $CDCl_3$): δ 1.34 (s, 9H), 2.47 (d, 3H), 2.55 (d, 3H), 2.70 (d, 3H), 4.42 (d, 2H), 6.76 (m, 1H), 7.36 (m, 1H), 7.54 (m, 1H), 7.75 (m, 2H), 7.98 (m, 1H), 8.25 (m, 1H)

ES-MS m/z: 477.60 $[M+H]^+$

Preparation Example 4-3: N-(6-methoxy-5-(1-methyl-7-(methylthio)-2-oxo-1,2-dihydropyrimido [4,5-d]pyrimidin-3(4H)-yl)pyridin-3-yl)-3- (trifluoromethyl)benzamide (V-3)

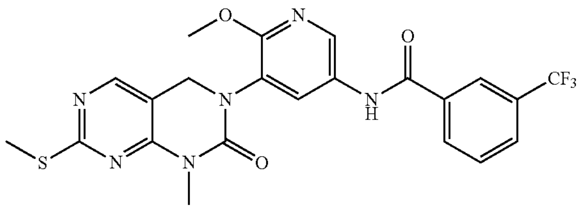 [SMILES: COc1ncc(NC(=O)c2cccc(C(F)(F)F)c2)cc1N1Cc2cnc(SC)nc2N(C)C1=O]

0.10 g (95%) of the title compound was obtained in the same manner as in Preparation Example 4-1 using the compound (IV-3) (0.10 g, 0.21 mmol) prepared in Preparation Example 3-4 instead of the compound (IV-1).

$^1$H NMR (400 MHz, $CDCl_3$): δ 2.55 (s, 3H), 3.34 (d, 3H), 4.25 (s, 3H), 5.06 (s, 2H), 6.88 (dd, 1H), 7.31-7.42 (m, 2H), 7.65-7.95 (m, 4H), 8.06 (d, 1H), 8.12 (s, 1H)

ES-MS m/z: 505.09 $[M+H]^+$

Preparation Example 4-4: 4-(4,4-dimethyl-4,5-dihydrooxazol-2-yl)-N-(6-methyl-5-(1-methyl-7-(methylthio))-2-oxo-1,2-dihydropyrimido[4,5-d]pyrimidin-3 (4H)-yl)pyridin-3-yl)benzamide (V-4)

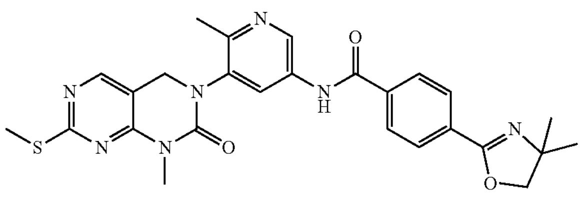

0.32 g (76%) of the title compound was obtained in the same manner as in Preparation Example 4-1 using the compound (IV-4) (0.40 g, 0.81 mmol) prepared in Preparation Example 3-5 instead of the compound (IV-1).

ES-MS m/z: 518.09 $[M+H]^+$

Preparation Example 4-5: 3-(4,4-dimethyl-4,5-dihydrooxazol-2-yl)-N-(6-methyl-5-(1-methyl-7-(methylthio)-2-oxo-1,2-dihydropyrimido[4,5-d]pyrimidin-3 (4H)-yl)pyridin-3-yl)benzamide (V-5)

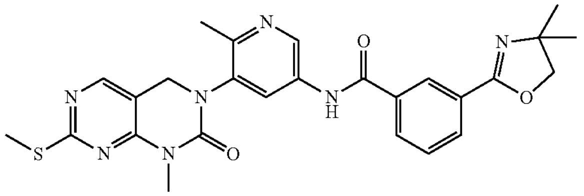

0.35 g (83%) of the title compound was obtained in the same manner as in Preparation Example 4-1 using the compound (IV-5) (0.40 g, 0.81 mmol) prepared in Preparation Example 3-6 instead of the compound (IV-1).

ES-MS m/z: 518.09 $[M+H]^+$

Preparation Example 4-6: 3-(t-butyl)-N-(6-methoxy-5-(1-methyl-7-(methylthio)-2-oxo-1,2-dihydropyrimido[4,5-d]pyrimidin-3(4H)-yl)pyridin-3-yl)benzamide (V-6)

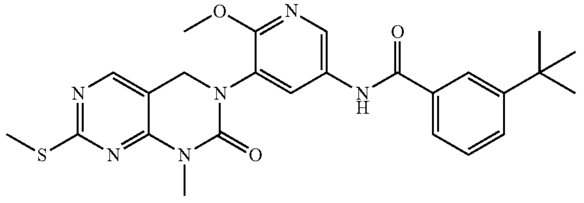 [SMILES: COc1ncc(NC(=O)c2cccc(C(C)(C)C)c2)cc1N1Cc2cnc(SC)nc2N(C)C1=O]

0.17 g (90%) of the title compound was obtained in the same manner as in Preparation Example 4-1 using the compound (IV-6) (0.18 g, 0.39 mmol) prepared in Preparation Example 3-7 instead of the compound (IV-1).

ES-MS m/z: 493.62 $[M+H]^+$

Preparation Example 4-7: 3-(4,4-dimethyl-4,5-dihydrooxazol-2-yl)-N-(6-methoxy-5-(1-methyl-7-(methylthio)-2-oxo-1,2-dihydropyrimido[4,5-d]pyrimidin-3(4H)-yl)pyridin-3-yl)benzamide (V-7)

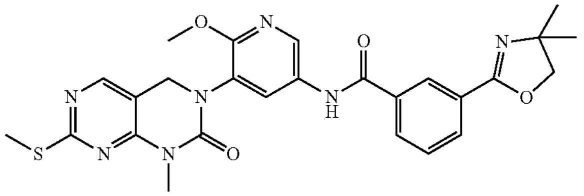

0.15 g (93%) of the title compound was obtained in the same manner as in Preparation Example 4-1 using the compound (IV-7) (0.15 g, 0.30 mmol) prepared in Preparation Example 3-8 instead of the compound (IV-1).

ES-MS m/z: 534.65 $[M+H]^+$

Preparation Example 4-8: N-(6-chloro-5-(1-methyl-7-(methylthio)-2-oxo-1,2-dihydropyrimido[4,5-d]pyrimidin-3(4H)-yl)pyridin-3-yl)-3- (trifluoromethyl)benzamide (V-8)

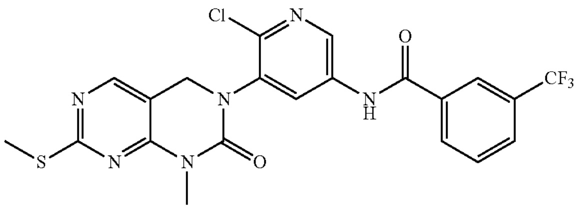

0.27 g (96%) of the title compound was obtained in the same manner as in Preparation Example 4-1 using the compound (IV-8) (0.27 g, 0.56 mmol) prepared in Preparation Example 3-9 instead of the compound (IV-1).

Preparation Example 4-9: 3-(t-butyl)-N-(6-chloro-5-(1-methyl-7-(methylthio)-2-oxo-1,2-dihydropyrimido[4,5-d]pyrimidin-3(4H)-yl)pyridin-3-yl)benzamide (V-9)

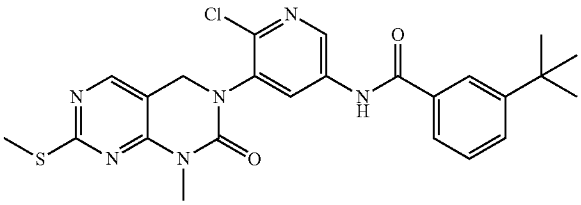 [SMILES: CSc1ncc2c(n1)N(C)C(=O)N(c1cc(NC(=O)c3cccc(C(C)(C)C)c3)cnc1Cl)C2]

0.23 g (78%) of the title compound was obtained in the same manner as in Preparation Example 4-1, using the compound (IV-9) (0.28 g, 0.59 mmol) prepared in Preparation Example 3-10 instead of the compound (IV-1).

Preparation Example 4-10: 2-(t-butyl)-N-(6-chloro-5-(1-methyl-7-(methylthio)-2-oxo-1,2-dihydropyrimido[4,5-d]pyrimidin-3(4H)-yl)pyridin-3-yl)thiazole-4-carboxamide (V-10)

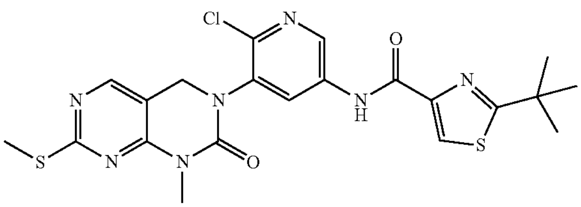 [SMILES: CSc1ncc2c(n1)N(C)C(=O)N(c1cc(NC(=O)c3csc(C(C)(C)C)n3)cnc1Cl)C2]

0.25 g (77%) of the title compound was obtained in the same manner as in Preparation Example 4-1 using the compound (IV-10) (0.31 g, 0.65 mmol) prepared in Preparation Example 3-11 instead of the compound (IV-1).

PREPARATION EXAMPLE 5

Preparation of the Compound of Formula (VI)

Preparation Example 5-1: N-(6-methyl-5-(1-methyl-7-(methylsulfonyl)-2-oxo-1,2-dihydropyrimido[4,5-d]pyrimidin-3(4H)-yl)pyridin-3-yl)-3- (trifluoromethyl)benzamide (VI-1)

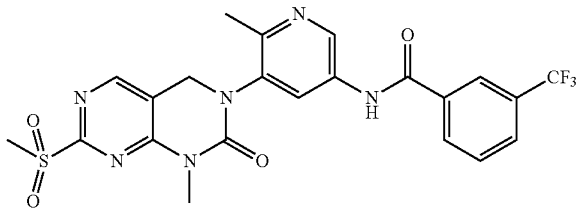 [SMILES: Cc1ncc(NC(=O)c2cccc(C(F)(F)F)c2)cc1N1Cc2cnc(S(C)(=O)=O)nc2N(C)C1=O]

The compound (V-1) (0.37 g, 0.76 mmol) prepared in Preparation Example 4-1 was dissolved in tetrahydrofuran: distilled water (2:1, 30 mL), oxone (4.66 g, 7.57 mmol) was added as an oxidizing agent, and the mixture was stirred at 65° C. for 5 hours. After the reaction was completed, the reaction solvent was evaporated under reduced pressure, washed sequentially with ethyl acetate, water, and brine, and the organic layer was dried over anhydrous sodium sulfate and concentrated under reduced pressure. The concentrated residue was purified by column chromatography to give 0.17 g (44%) of the title compound.

$^1$H NMR (400 MHz, $CDCl_3$): δ 2.70 (s, 3H), 3.38 (s, 3H), 3.40 (s, 3H), 4.42 (d, 2H), 6.76 (m, 1H), 7.36 (m, 1H), 7.48-7.99 (m, 4H), 8.25 (m, 1H), 9.12(s, 1H)

ES-MS m/z: 521.60 $[M+H]^+$

Preparation Example 5-2: 3-(t-butyl)-N-(6-methyl-5-(1-methyl-7-(methylsulfonyl)-2-oxo-1,2-dihydropyrimido[4,5-d]pyrimidin-3(4H)-yl)pyridin-3-yl) benzamide (VI-2)

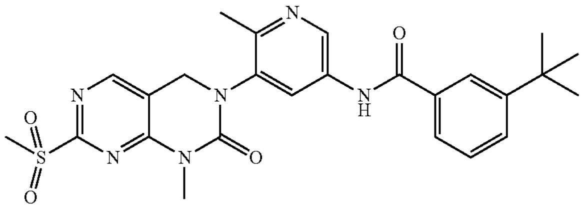 [SMILES: Cc1ncc(NC(=O)c2cccc(C(C)(C)C)c2)cc1N1Cc2cnc(S(C)(=O)=O)nc2N(C)C1=O]

0.22 g (42%) of the title compound was obtained in the same manner as in Preparation Example 5-1 using the compound (V-2) (0.51 g, 1.07 mmol) prepared in Preparation Example 4-2 instead of the compound (V-1).

$^1$H NMR (400 MHz, $CDCl_3$): δ 1.34 (s, 9H), 2.70 (s, 3H), 3.38 (s, 3H), 3.40 (s, 3H), 4.42 (d, 2H), 6.76 (m, 1H), 7.36 (m, 1H), 7.54 (m, 1H), 7.75 (m, 2H), 7.98 (m, 1H), 8.25 (m, 1H), 9.15(s, 1H)

ES-MS m/z: 509.72 $[M+H]^+$

Preparation Example 5-3: N-(6-methoxy-5-(1-methyl-7-(methylsulfonyl)-2-oxo-1,2-dihydropyrimido[4,5-d]pyrimidin-3(4H)-yl)pyridin-3-yl)-3-(trifluoromethyl)b enzamide (VI-3)

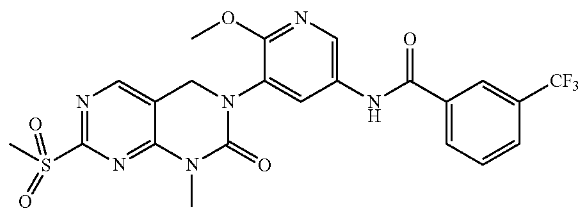 [SMILES: COc1ncc(NC(=O)c2cccc(C(F)(F)F)c2)cc1N1Cc2cnc(S(C)(=O)=O)nc2N(C)C1=O]

90 mg (97%) of the title compound was obtained in the same manner as in Preparation Example 5-1 using the compound (V-3) (0.09 g, 0.17 mmol) prepared in Preparation Example 4-3 instead of the compound (V-1).

$^1$H NMR (400 MHz, $CDCl_3$): δ 3.10 (s, 3H), 3.45 (s, 3H), 4.63 (s, 3H), 5.51(s, 2H), 6.56 (dd, 1H), 7.13-7.81 (m, 3H), 8.16-8.17 (m, 2H), 8.28 (d, 1H), 9.10 (s, 1H)

ES-MS m/z: 537.01 $[M+H]^+$

Preparation Example 5-4: 4-(4,4-dimethyl-4,5-dihydrooxazol-2-yl)-N-(6-methyl-5-(1-methyl-7-(methylsulfonyl))-2-oxo-1,2-dihydropyrimido[4,5-d]pyrimidin-3(4H)-yl)pyridin-3-yl)benzamide (VI-4)

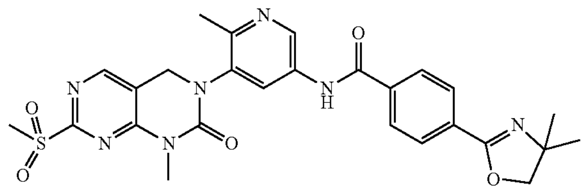

0.24 g (76%) of the title compound was obtained in the same manner as in Preparation Example 5-1 using the compound (V-4) (0.30 g, 0.58 mmol) prepared in Preparation Example 4-4 instead of the compound (V-1).

ES-MS m/z: 550.25 $[M+H]^+$

Preparation Example 5-5: 3-(4,4-dimethyl-4,5-dihydrooxazol-2-yl)-N-(6-methyl-5-(1-methyl-7-(methylsulfonyl)-2-oxo-1,2-dihydropyrimido[4,5-d]pyrimidin-3(4H)-yl)pyridin-3-yl)benzamide (VI-5)

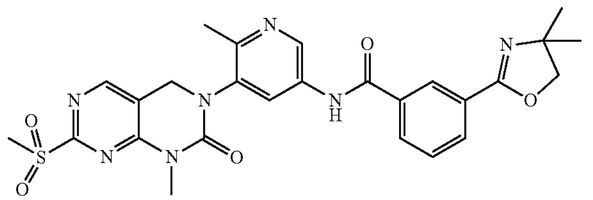

0.24 g (76%) of the title compound was obtained in the same manner as in Preparation Example 5-1 using the compound (V-5) (0.35 g, 0.58 mmol) prepared in Preparation Example 4-5 instead of the compound (V-1).

ES-MS m/z: 550.21 $[M+H]^+$

Preparation Example 5-6: 3-(t-butyl)-N-(6-methoxy-5-(1-methyl-7-(methylsulfonyl)-2-oxo-1,2-dihydropyrimido[4,5-d]pyrimidin-3(4H)-yl)pyridin-3-yl)benzamide (VI-6)

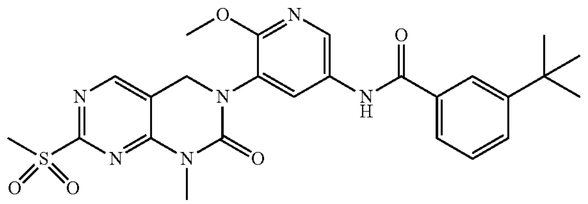 [SMILES: COc1ncc(NC(=O)c2cccc(C(C)(C)C)c2)cc1N1Cc2cnc(S(C)(=O)=O)nc2N(C)C1=O]

0.17 g (91%) of the title compound was obtained in the same manner as in Preparation Example 5-1 using the compound (V-6) (0.17 g, 0.35 mmol) prepared in Preparation Example 4-6 instead of the compound (V-1).

$^1$H NMR (400 MHz, $CDCl_3$): δ 1.36 (s, 9H), 3.37 (s, 3H), 3.90 (s, 3H), 4.82 (s, 2H), 7.41 (t, 1H), 7.60 (d, 1H), 7.66 (d, 1H), 7.94 (s, 1H), 8.21 (dd, 1H), 8.24 (s, 1H), 8.38 (t, 1H)

ES-MS m/z: 525.61 $[M+H]^+$

Preparation Example 5-7: 3-(4,4-dimethyl-4,5-dihydrooxazol-2-yl)-N-(6-methoxy-5-(1-methyl-7-(methylsulfonyl)-2-oxo-1,2-dihydropyrimido[4,5-d]pyrimidin-3(4H)-yl)pyridin-3-yl)benzamide (VI-7)

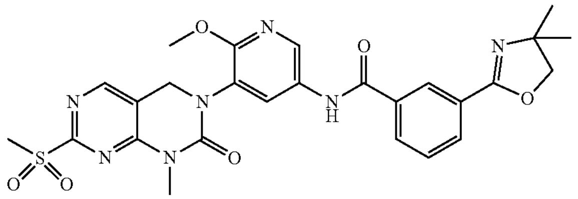

0.14 g (89%) of the title compound was obtained in the same manner as in Preparation Example 5-1 using the compound (V-7) (0.15 g, 0.28 mmol) prepared in Preparation Example 4-7 instead of the compound (V-1).

ES-MS m/z: 566.50 $[M+H]^+$

Preparation Example 5-8: N-(6-chloro-5-(1-methyl-7-(methylsulfonyl)-2-oxo-1,2-dihydropyrimido[4,5-d]pyrimidin-3(4H)-yl)pyridin-3-yl)-3- (trifluoromethyl)benzamide (VI-8)

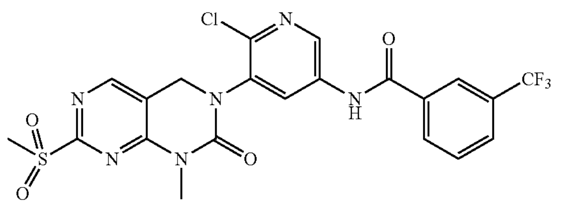 [SMILES: CN1C(=O)N(c2cc(NC(=O)c3cccc(C(F)(F)F)c3)cnc2Cl)Cc2cnc(S(C)(=O)=O)nc21]

0.21 g (77%) of the title compound was obtained in the same manner as in Preparation Example 5-1 using the compound (V-8) (0.26 g, 0.51 mmol) prepared in Preparation Example 4-8 instead of the compound (V-1).

Preparation Example 5-9: 3-(t-butyl)-N-(6-chloro-5-(1-methyl-7-(methylsulfonyl)-2-oxo-1,2-dihydropyrimido[4,5-d]pyrimidin-3(4H)-yl)pyridin-3-yl)benzamide (VI-9)

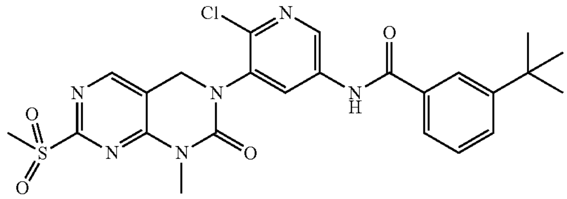 [SMILES: CN1C(=O)N(c2cc(NC(=O)c3cccc(C(C)(C)C)c3)cnc2Cl)Cc2cnc(S(C)(=O)=O)nc21]

0.21 g (86%) of the title compound was obtained in the same manner as in Preparation Example 5-1 using the compound (V-9) (0.23 g, 0.46 mmol) prepared in Preparation Example 4-9 instead of the compound (V-1).

Preparation Example 5-10: 2-(t-butyl)-N-(6-chloro-5-(1-methyl-7-(methylsulfonyl)-2-oxo-1,2-dihydropyrimido[4,5-d]pyrimidin-3(4H)-yl)pyridin-3-yl) thiazole- 4-carboxamide (VI-10)

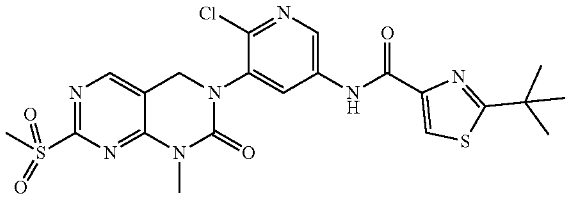 [SMILES: CN1C(=O)N(c2cc(NC(=O)c3csc(C(C)(C)C)n3)cnc2Cl)Cc2cnc(S(C)(=O)=O)nc21]

0.19 g (67%) of the title compound was obtained in the same manner as in Preparation Example 5-1 using the compound (V-10) (0.26 g, 0.52 mmol) prepared in Preparation Example 4-10 instead of the compound (V-1).

EXAMPLE

Preparation of the Compound of Formula (I)

Example 1: N-(6-methyl-5-(1-methyl-2-oxo-7-(phenylamino)-1,2-dihydropyrimido[4,5-d]pyrimidin-3 (4H)-yl)pyridin-3-yl)-3- (trifluoromethyl)benzamide (I-1)

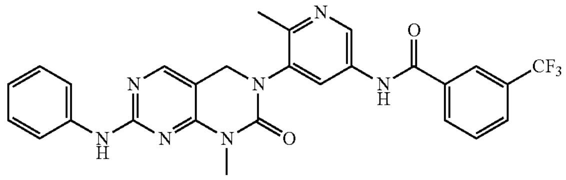 [SMILES: Cc1ncc(NC(=O)c2cccc(C(F)(F)F)c2)cc1N1Cc2cnc(Nc3ccccc3)nc2N(C)C1=O]

The compound (VI-1) (0.17 g, 0.33 mmol) prepared in Preparation Example 5-1 was dissolved in 10 ml of 1,4-dioxane, added to 4 ml of aniline, and stirred at 100° C. for 3 hours. After the reaction was completed, extraction was sequentially performed with ethyl acetate, water and brine, and the organic layer was dried over anhydrous sodium sulfate and concentrated under reduced pressure. The concentrated residue was purified by column chromatography to give 87 mg (50%) of the title compound.

$^1$H NMR (400 MHz, DMSO-$d_6$): δ 2.55 (s, 3H), 3.09 (s, 3H), 4.42 (d, 2H), 6.46-7.54 (m, 6H), 7.75 (m, 2H), 8.01 (m, 1H), 8.17 (m, 1H), 9.60 (s, 1H), 10.36 (s, 1H)

ES-MS m/z: 534.62 $[M+H]^+$

Example 2: 3-(t-butyl)-N-(6-methyl-5-(1-methyl-2-oxo-7-(phenylamino)-1,2-dihydropyrimido[4,5-d] pyrimidin-3(4H)-yl)pyridin-3-yl)benzamide (I-2)

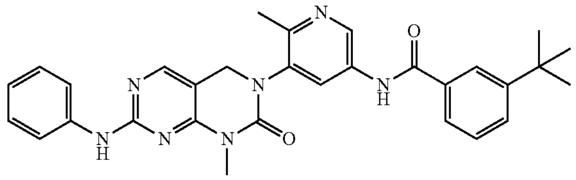

86 mg (40%) of the title compound was obtained in the same manner as in Example 1 using the compound (VI-2) (0.21 g, 0.41 mmol) prepared in Preparation Example 5-2 instead of the compound (VI-1).

$^1$H NMR (400 MHz, DMSO-$d_6$): δ 1.34 (s, 9H), 2.55 (s, 3H), 3.11 (s, 3H), 4.42 (d, 2H), 6.46-7.54 (m, 9H), 7.75 (m, 1H), 7.98 (m, 1H), 8.25 (m, 1H), 9.53 (s, 1H), 10.35 (s, 1H)

ES-MS m/z: 522.72 $[M+H]^+$

Example 3: N-(6-methoxy-5-(1-methyl-2-oxo-7-(phenylamino)-1,2-dihydropyrimido[4,5-d]pyrimidin-3(4H)-yl)pyridin-3-yl)-3- (trifluoromethyl)benzamide (I-3)

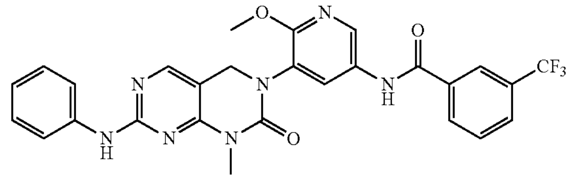 [SMILES: COc1ncc(NC(=O)c2cccc(C(F)(F)F)c2)cc1N1Cc2cnc(Nc3ccccc3)nc2N(C)C1=O]

25 mg (27%) of the title compound was obtained in the same manner as in Example 1 using the compound (VI-3) (90 mg, 0.17 mmol) prepared in Preparation Example 5-3 instead of the compound (VI-1).

$^1$H NMR (400 MHz, DMSO-$d_6$): 3.35 (s, 3H), δ 3.90 (s, 3H), 4.63 (s, 2H), 6.95 (t, 1H), 7.29 (t, 1H), 7.70 (d, 2H), 7.79 (t, 2H), 8.00 (d, 1H), 8.16-8.17 (m, 2H), 8.28 (d, 1H), 8.33 (s, 1H), 8.51 (s, 1H), 9.60 (s, 1H), 10.67 (s, 1H)

ES-MS m/z: 550.07 $[M+H]^+$

Example 4: 4-(4,4-dimethyl-4,5-dihydrooxazol-2-yl)-N-(6-methyl-5-(1-methyl-2-oxo-7-(phenylamino)-1,2-dihydropyrimido[4,5-d]pyrimidin-3(4H)-yl)pyridin-3-yl)benzamide (I-4)

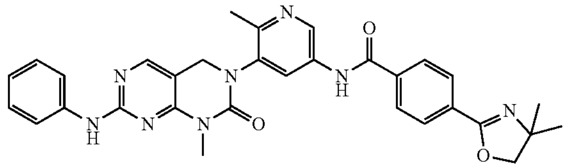 [SMILES: Cc1ncc(NC(=O)c2ccc(C3=NC(C)(C)CO3)cc2)cc1N1Cc2cnc(Nc3ccccc3)nc2N(C)C1=O]

0.10 g (55%) of the title compound was obtained in the same manner as in Example 1 using the compound (VI-4) (0.20 g, 0.36 mmol) prepared in Preparation Example 5-4 instead of the compound (VI-1).

$^1$H NMR (400 MHz, DMSO-$d_6$): δ 1.31 (s, 6H), 2.89 (d, 3H), 3.36 (s, 3H), 4.16 (s, 2H), 4.61 (d, 1H), 4.73 (d, 1H), 7.12-7.23 (m, 5H), 7.83 (t, 1H), 8.03 (d, 1H), 8.29 (d, 1H), 8.37 (s, 1H), 8.56 (d, 1H), 8.66 (s, 1H), 8.77 (s, 1H), 9.53 (s, 1H), 10.98 (s, 1H)

ES-MS m/z: 563.72 [M+H]$^+$

Example 5: 3-(4,4-dimethyl-4,5-dihydrooxazol-2-yl)-N-(6-methyl-5-(1-methyl-2-oxo-7-(phenylamino)-1,2-dihydropyrimido[4,5-d]pyrimidin-3(4H)-yl)pyridin-3-yl)benzamide (I-5)

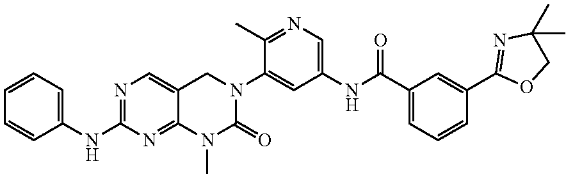 [SMILES: Cc1ncc(NC(=O)c2cccc(C3=NC(C)(C)CO3)c2)cc1N1Cc2cnc(Nc3ccccc3)nc2N(C)C1=O]

0.14 g (58%) of the title compound was obtained in the same manner as in Example 1 using the compound (VI-5) (0.23 g, 0.42 mmol) prepared in Preparation Example 5-5 instead of the compound (VI-1).

$^1$H NMR (400 MHz, DMSO-$d_6$): δ 1.41 (s, 6H), 2.59 (d, 3H), 3.36 (s, 3H), 4.13 (s, 2H), 4.61 (d, 1H), 4.73 (d, 1H), 7.12-7.23 (m, 5H), 7.81 (s, 1H), 8.03 (d, 1H), 8.29 (d, 1H), 8.37 (s, 1H), 8.56 (d, 1H), 8.66 (s, 1H), 8.77 (s, 1H), 9.53 (s, 1H), 10.98 (s, 1H)

ES-MS m/z: 563.62 [M+H]$^+$

Example 6: 3-(t-b utyl)-N-(6-methoxy-5-(1-methyl-2-oxo-7-(phenylamino)-1,2-dihydropyrimido[4,5-d]pyrimidin-3(4H)-yl)pyridin-3-yl)benzamide (I-6)

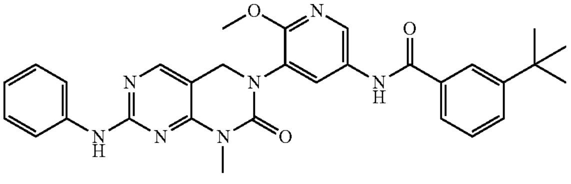 [SMILES: COc1ncc(NC(=O)c2cccc(C(C)(C)C)c2)cc1N1Cc2cnc(Nc3ccccc3)nc2N(C)C1=O]

83 mg (47%) of the title compound was obtained in the same manner as in Example 1 using the compound (VI-6) (0.17 g, 0.32 mmol) prepared in Preparation Example 5-6 instead of the compound (VI-1).

$^1$H NMR (400 MHz, DMSO-$d_6$): δ 1.34 (s, 9H), 3.37 (s, 3H), 3.90 (s, 3H), 4.63 (d, 2H), 6.95 (t, 1H), 7.29 (t, 1H), 7.47 (t, 1H), 7.64 (d, 1H), 7.76-7.81 (m, 2H), 7.96 (t, 1H), 8.14 (d, 1H), 8.16 (s, 1H), 8.52(d, 1H), 9.59 (s, 1H), 10.38 (s, 1H)

ES-MS m/z: 538.64 [M+H]$^+$

Example 7: 3-(4,4-dimethyl-4,5-dihydrooxazol-2-yl)-N-(6-methoxy-5-(1-methyl-2-oxo-7-(phenylamino)-1,2-dihydropyrimido[4,5-d]pyrimidin-3(4H)-yl)pyridin-3-yl)benzamide (I-7)

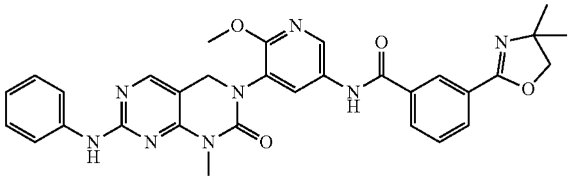 [SMILES: COc1ncc(NC(=O)c2cccc(C3=NC(C)(C)CO3)c2)cc1N1Cc2cnc(Nc3ccccc3)nc2N(C)C1=O]

65 mg (44%) of the title compound was obtained in the same manner as in Example 1 using the compound (VI-7) (0.14 g, 0.25 mmol) prepared in Preparation Example 5-7 instead of the compound (VI-1).

$^1$H NMR (400 MHz, DMSO-$d_6$): δ 1.34 (s, 9H), 3.37 (s, 3H), 3.90 (s, 3H), 4.15(s, 2H), 4.63 (d, 1H), 4.71 (d, 1H), 6.95 (t, 1H), 7.29 (t, 1H), 7.47 (t, 1H), 7.64 (d, 1H), 7.78-7.85 (m, 2H), 8.01-8.12 (m, 2H), 8.35 (t, 1H), 8.56 (d, 1H), 8.66 (s, 1H), 8.77 (s, 1H), 9.57 (s, 1H), 10.98 (s, 1H)

ES-MS m/z: 579.65 [M+H]$^+$

Example 8: N-(6-chloro-5-(1-methyl-2-oxo-7-(phenylamino)-1,2-dihydropyrimido[4,5-d]pyrimidin-3(4H)-yl)pyridin-3-yl)-3- (trifluoromethyl)benzamide (I-8)

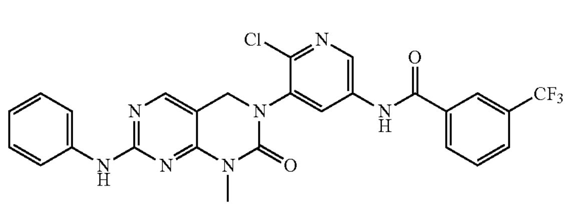 [SMILES: CN1C(=O)N(c2cc(NC(=O)c3cccc(C(F)(F)F)c3)cnc2Cl)Cc2cnc(Nc3ccccc3)nc21]

92 mg (46%) of the title compound was obtained in the same manner as in Example 1 using the compound (VI-8) (0.20 g, 0.37 mmol) prepared in Preparation Example 5-8 instead of the compound (VI-1).

$^1$H NMR (400 MHz, DMSO-$d_6$): δ 3.33 (s, 3H), 4.59-4.74 (m, 2H), 6.91 (t, 1H), 7.25 (t, 2H), 7.72-7.81 (m, 3H), 7.99 (d, 1H), 8.15 (s, 1H), 8.26 (m, 2H), 8.46 (s, 1H), 8.73 (s, 1H), 9.59 (s, 1H), 10.92 (s, 1H)

ES-MS m/z: 553.97 [M+H]$^+$

Example 9: 3-(t-butyl)-N-(6-chloro-5-(1-methyl-2-oxo-7-(phenylamino)-1,2-dihydropyrimido[4,5-d]pyrimidin-3(4H)-yl)pyridin-3-yl)benzamide (I-9)

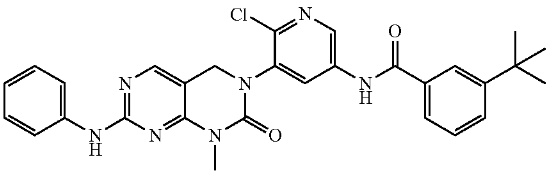 [SMILES: CN1C(=O)N(c2cc(NC(=O)c3cccc(C(C)(C)C)c3)cnc2Cl)Cc2cnc(Nc3ccccc3)nc21]

98.3 mg (46%) of the title compound was obtained in the same manner as in Example 1 using the compound (VI-9) (0.21 g, 0.40 mmol) prepared in Preparation Example 5-9 instead of the compound (VI-1).

$^1$H NMR (400 MHz, DMSO-$d_6$): δ 1.31 (s, 9H), 3.33 (s, 3H), 4.59-4.74 (m, 2H), 6.91 (t, 1H), 7.26 (t, 2H), 7.46 (t, 1H), 7.63 (d, 1H), 7.72-7.79 (m, 3H), 7.79 (s, 1H), 8.15 (s, 1H), 8.44 (d, 1H), 8.75 (d, 1H), 9.58 (s, 1H), 10.65 (s, 1H)

ES-MS m/z: 542.14 [M+H]$^+$

Example 10: 2-(t-butyl)-N-(6-chloro-5-(1-methyl-2-oxo-7-(phenylamino)-1,2-dihydropyrimido[4,5-d]pyrimidin-3(4H)-yl)pyridin-3-yl)thiazole-4-carboxamide (I-10)

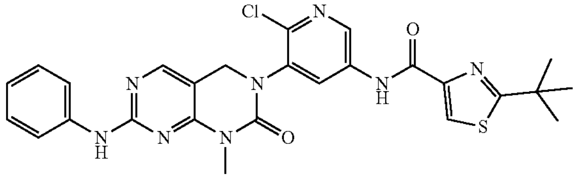 [SMILES: CN1C(=O)N(c2cc(NC(=O)c3csc(C(C)(C)C)n3)cnc2Cl)Cc2cnc(Nc3ccccc3)nc21]

0.12 g (64%) of the title compound was obtained in the same manner as in Example 1 using the compound (VI-10) (0.18 g, 0.33 mmol) prepared in Preparation Example 5-10 instead of the compound (VI-1).

$^1$H NMR (400 MHz, DMSO-$d_6$): δ 1.47 (s, 9H), 3.37 (s, 3H), 4.62-4.77 (m, 2H), 6.95 (t, 1H), 7.27-7.31 (t, 2H), 7.78 (d, 2H), 8.18 (s, 1H), 8.39 (s, 1H), 8.51 (d, 1H), 8.90 (d, 1H), 9.62 (s, 1H), 10.43 (s, 1H)

ES-MS m/z: 549.16 [M+H]$^+$

Example 11: N-(6-chloro-5-(7-((4-hydroxyphenyl)amino)-1-methyl-2-oxo-1,2-dihydropyrimido[4,5-d]pyrimidin-3(4H)-yl)pyridin-3-yl)-3- (trifluoromethyl)benzamide (I-11)

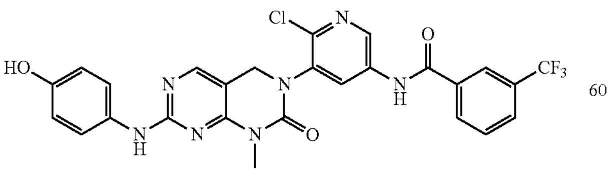

The compound (VI-8) (1.00 g, 1.85 mmol) prepared in Preparation Example 5-8 instead of the compound (VI-1) was dissolved in 20 ml of 1,4-dioxane, and 4-aminophenol (1.00 g, 9.24 mmol) and trifluoroacetic acid (0.71 mL, 9.24 mmol) were added and stirred at 85° C. for 7 hours. After the reaction was completed, the reaction solvent was removed, methanol was added, and the mixture was refluxed for 2 hours to give 0.63 g (60%) of the title compound.

$^1$H NMR (400 MHz, DMSO-$d_6$): δ 3.33 (s, 3H), 4.58-4.74 (m, 2H), 6.68-6.72 (m, 2H), 7.47-7.50 (m, 2H), 7.81-7.85 (m, 1H), 8.01-8.03 (m, 1H), 8.11 (s, 1H), 8.28-8.34 (m, 2H), 8.47 (d, 1H), 8.77 (d, 1H), 9.05 (s, 1H), 9.29 (s, 1H), 10.95 (s, 1H)

ES-MS m/z: 569.16 [M+H]$^+$

EXPERIMENTAL EXAMPLE 1

Analysis of PD-L1 Expression Inhibiting Activity

The PD-L1 promoter gene region was inserted into the pGL4.14-[luc2/Hygro] vector (promega, Madison, WI) in the following way to prepare a promoter-reporter construct for measuring gene transcription activity.

After preparing primer including KpnI and XhoI restriction enzyme sites in PD-L1, PCR (polymerase chain reaction) was performed, and promoter region DNA was separated by performing electrophoresis on an agarose gel. The pGL4.14-[1uc2/Hygro] vector containing firefly luciferase as a reporter gene was treated with the same restriction enzyme, and separated by agarose gel electrophoresis and gel extraction. The pure isolated PD-L1 promoter gene region and the pGL4.14-[luc2/Hygro] vector were reacted at 50° C. for 1 hour using in-fusion DNA ligase (Takara), followed by *E. coli* transformation to prepare a promoter-reporter construct into which the PCSK9 promoter was inserted, which was named pGL4.14-PD-L1.

To measure the transcriptional activity of the PD-L1 gene promoter, A549 cells were transiently transfected with the PD-L1 promoter-reporter construct as follows, and then the luciferase activity of the cell extract was measured.

The DNA-lipofectamine complex was prepared according to the manufacturer's protocol using 0.1 μtg of promoter-reporter construct plasmid and Lipofectamine 2000 reagent (Invitrogen). Opti-MEM medium (Invitrogen) was used in the process of forming a complex between DNA and Lipofectamine 2000. A549 cells were prepared at 2.5x10$^5$ cells per well (1 ml) in a 12-well plate by checking the number of cells immediately before adding the DNA. The DNA-lipofectamine complex was carefully mixed with A549 cells and reacted in an incubator at 37° C. for 6 hours. Thereafter, the medium was changed to search for transfected cells, and PD-L1-transfected A549 cells were found through a luciferase test. This was named A549 pGL4.14-PD-L1 cell line and the experiment was conducted. IFNγ (50 ng/ml) was used as a PD-L1 inducer.

PD-L1 expression condition was established using EGF and IFNγ known to induce PD-L1 in Beas-2B cells, a human normal lung epithelial cell line. At the RNA level, when EGF was treated at concentrations of 25, 50, and 100 ng/ml, PD-L1 activation was not observed, and only IFNγ increased PD-L1. In addition, the mRNA level of PD-L1 increased from 2 hours after treatment with 50ng/ml of IFNγ, and finally, the mRNA level increased most distinctly 4 hours after treatment with 50ng/ml of IFNγ.

Likewise, as a result of confirming the protein level of PD-L1 in Beas-2B cells, when IFNγ was treated, there was no significant change before 8 hours, but the amount of PD-L1expression increased after 8 hours. Therefore, 20 hours after treatment with 50 ng/ml of IFNγ, the protein was lysed and used.

The A549 pGL4.14-PD-L1 cell line was treated with the pyrimido pyrimidinone derivatives of Example at concentrations of 0.1 μM and 1.0 μM, respectively, and PD-L1 expression inhibition was evaluated using a luminometer. For comparison, the same experiment was performed for GS9973 (Entospletinib) known to have PD-L1 expression inhibitory activity.

The inhibition rate of PD-L1 expression was calculated by Equation 1 below.

$$PD\text{-}L1 \text{ expression inhibition rate } (\%) = 100 - [(A/B) \times 100] \quad \text{[Equation 1]}$$

wherein, A is a value when treated with a drug, and B is a value when not treated with a drug.

The results are shown in Table 1 below.

TABLE 1

| | PD-L1 expression inhibition rate in A549 (%) | |
|---|---|---|
| | 0.1 μM | 1.0 μM |
| GS9973(Entospletinib) | 10.3 | 47.1 |
| I-1 | 12.8 | 87.1 |
| I-2 | 32.6 | 72.5 |
| I-3 | 29.3 | 92.5 |
| I-4 | 20.1 | 82.5 |
| I-5 | 19.4 | 81.9 |
| I-6 | 13.9 | 94.1 |
| I-7 | 13.1 | 85.3 |
| I-8 | 60.4 | 97.5 |
| I-9 | 48.8 | 97.2 |
| I-10 | 67.0 | 98.0 |
| I-11 | 65.0 | 98.0 |

From Table 1, it can be seen that the pyrimido pyrimidinone compound according to the present invention has superior PD-L1 expression inhibitory activity compared to GS9973 (Entospletinib), and that this PD-L1 expression inhibitory activity appears in a concentration-dependent manner.

EXPERIMENTAL EXAMPLE 2

In vivo Efficacy Evaluation of PD-L1 Expression Inhibitors

Melanoma B16F10 cells were subcutaneously injected into the cervical region of a 6-week-old male $C_{57}BL/6$ mouse at a concentration of $1\times10^6$ cells/100 μl to prepare a disease model. After the disease model was prepared, the next day was the first day of administration, and as shown in Table 2 below, it was orally administered once a day for 14 days, and the tumor was extracted on the 15th day of the test. Changes in tumor volume and tumor size were measured.

The results are shown in FIGS. 1 and 2.

TABLE 2

| | Group | Gender | Number of animals | Animal number | Dose (mg/kg) |
|---|---|---|---|---|---|
| G1 | Normal control | M | 8 | 1~8 | — |
| G2 | I-8 | M | 8 | 9~16 | 10 |
| G3 | I-9 | M | 8 | 17~24 | 10 |
| G4 | I-2 | M | 8 | 25~32 | 20 |
| G5 | I-3 | M | 8 | 33~40 | 20 |

From FIGS. 1 to 2, it can be seen that compounds 1-2, 1-3, 1-8 and 1-9 have tumor growth inhibition ability of 22 to 59% compared to the control group.

EXPERIMENTAL EXAMPLE 3

Western-Blot Analysis

Experimental Example 3-1

After the in vivo tumor inhibition test using compound 1-8 of Experimental Example 2, the PD-L1 expression inhibition effect in tumor cells extracted from mice was confirmed through Western-blot analysis. For comparison, the efficacy of inhibiting PD-L1 expression in tumor cells extracted from the control mice was also confirmed through Western-blot analysis.

Proteins were identified with the ChemiDoc™ imaging system (Bio-rad) using a chemiluminescence (ECL) kit (elpis biotec, EBP-1073). The results are shown in FIG. 3.

From FIG. 3, it can be seen that the expression of PD-L1 is reduced when compound 1-8 is administered compared to the control group.

Experimental Example 3-2

After treating PD-L1 overexpressing cells with the example compounds, the PD-L1 expression inhibitory effect was confirmed through Western-blot analysis.

To examine the change in PD-L1 protein level, NCI-H358 (NSCLC) cell line was seeded at $6\times10^5$ cells/ml. After 24 hours, the NCI-H358 (NSCLC) cell line was treated with IFN-γ (20 ng/ml) to overexpress PD-L1, and 24 hours later, the compound was additionally treated at 1 μM and 10 μM, respectively. After 24 hours, proteins were identified with ChemiDoc™ imaging system (Bio-rad) using a chemiluminescence (ECL) kit (elpis biotec, EBP-1073). Western-blot analysis results are shown in FIG. 4.

From FIG. 4, it can be confirmed that the example compounds exhibit an inhibitory effect on PD-L1 expression in a concentration-dependent manner compared to the control group which was not treated with the drug.

The invention claimed is:

1. A pyrimido pyrimidinone compound of formula (I) or pharmaceutically acceptable salt thereof:

(I)

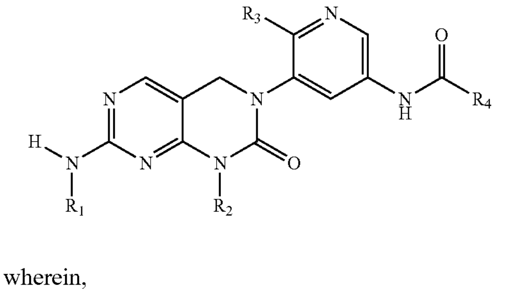

wherein, $R_1$ is phenyl unsubstituted or substituted with a halogen or hydroxyl;

$R_2$ is a $C_1$-$C_4$ alkyl;

$R_3$ is hydrogen, a halogen, a $C_1$-$C_4$ alkyl or a $C_1$-$C_4$ alkoxy; and $R_4$ is phenyl unsubstituted or substituted with a $C_1$-$C_4$ alkyl, a $C_1$-$C_4$ haloalkyl or an alkyldihydrooxazolyl, or an alkylthiazolyl.

2. The pyrimido pyrimidinone compound or pharmaceutically acceptable salt thereof according to claim 1, wherein, $R_1$ is phenyl, fluorophenyl or hydroxyphenyl;

$R_2$ is methyl;

$R_3$ is hydrogen, chloro, bromo, methyl or methoxy; and $R_4$ is trifluoromethylphenyl, t-butylphenyl, dimethyldihydrooxazolylphenyl or t-butylthiazolyl.

3. The pyrimido pyrimidinone compound or pharmaceutically acceptable salt thereof according to claim 1, wherein the pyrimido pyrimidinone compound is selected from the group consisting of the following compounds:

N-(6-methyl-5-(1-methyl-2-oxo-7-(phenylamino)-1,2-dihydropyrimido[4,5-d]pyrimidin-3(4H)-yl)pyridin-3-yl)-3-(trifluoromethyl)benzamide (I-1);

3-(t-butyl)-N-(6-methyl-5-(1-methyl-2-oxo-7-(phenylamino)-1,2-dihydropyrimido[4,5-d]pyrimidin-3(4H)-yl)pyridin-3-yl)benzamide (I-2);

N-(6-methoxy-5-(1-methyl-2-oxo-7-(phenylamino)-1,2-dihydropyrimido[4,5-d]pyrimidin-3(4H)-yl)pyridin-3-yl)-3-(trifluoromethyl)benzamide (I-3);

4-(4,4-dimethyl-4,5-dihydrooxazol-2-yl)-N-(6-methyl-5-(1-methyl-2-oxo-7-(phenylamino)-1,2-dihydropyrimido[4,5-d]pyrimidin-3(4H)-yl)pyridin-3-yl)benzamide (I-4);

3-(4,4-dimethyl-4,5-dihydrooxazol-2-yl)-N-(6-methyl-5-(1-methyl-2-oxo-7-(phenylamino)-1,2-dihydropyrimido[4,5-d]pyrimidin-3(4H)-yl)pyridin-3-yl)benzamide (I-5);

3-(t-butyl)-N-(6-methoxy-5-(1-methyl-2-oxo-7-(phenylamino)-1,2-dihydropyrimido[4,5-d]pyrimidin-3(4H)-yl)pyridin-3-yl)benzamide (I-6);

3-(4,4-dimethyl-4,5-dihydrooxazol-2-yl)-N-(6-methoxy-5-(1-methyl-2-oxo-7-(phenylamino)-1,2-dihydropyrimido[4,5-d]pyrimidin-3(4H)-yl)pyridin-3-yl)benzamide (I-7);

N-(6-chloro-5-(1-methyl-2-oxo-7-(phenylamino)-1,2-dihydropyrimido[4,5-d]pyrimidin-3(4H)-yl)pyridin-3-yl)-3-(trifluoromethyl)benzamide (I-8);

3-(t-butyl)-N-(6-chloro-5-(1-methyl-2-oxo-7-(phenylamino)-1,2-dihydropyrimido[4,5-d]pyrimidin-3(4H)-yl)pyridin-3-yl)benzamide (I-9);

2-(t-butyl)-N-(6-chloro-5-(1-methyl-2-oxo-7-(phenylamino)-1,2-dihydropyrimido[4,5-d]pyrimidin-3(4H)-yl)pyridin-3-yl)thiazole-4-carboxamide (I-10); and N-(6-chloro-5-(7-((4-hydroxyphenyl)amino)-1-methyl-2-oxo-1,2-dihydropyrimido[4,5-d]pyrimidin-3(4H)-yl)pyridin-3-yl)-3-(trifluoromethyl)benzamide (I-11).

4. A pharmaceutical composition comprising the pyrimido pyrimidinone compound or pharmaceutically acceptable salt thereof according to claim 1 together with a pharmaceutically acceptable carrier.

5. The pharmaceutical composition according to claim 4 for treating cancer.

6. The pharmaceutical composition according to claim 5 for treating colon cancer, lung cancer, breast cancer, gastric cancer, cervical cancer, bladder cancer, blood cancer or non-Hodgkin's lymphoma.

7. A method for inhibiting programmed death-ligand 1 (PD-L1) or treating cancer in a subject in need thereof, comprising administering to the subject an effective amount of a composition comprising the pyrimido pyrimidinone compound or pharmaceutically acceptable salt thereof according to claim 1.

8. The method according to claim 7, wherein the cancer is colon cancer, lung cancer, breast cancer, gastric cancer, cervical cancer, bladder cancer, blood cancer, or non-Hodgkin's lymphoma.

9. The method according to claim 7, wherein the pyrimido pyrimidinone compound or pharmaceutically acceptable salt thereof is selected from the group consisting of the following compounds:

N-(6-methyl-5-(1-methyl-2-oxo-7-(phenylamino)-1,2-dihydropyrimido[4,5-d]pyrimidin-3(4H)-yl)pyridin-3-yl)-3-(trifluoromethyl)benzamide (I-1);

3-(t-butyl)-N-(6-methyl-5-(1-methyl-2-oxo-7-(phenylamino)-1,2-dihydropyrimido[4,5-d]pyrimidin-3(4H)-yl)pyridin-3-yl)benzamide (I-2);

N-(6-methoxy-5-(1-methyl-2-oxo-7-(phenylamino)-1,2-dihydropyrimido[4,5-d]pyrimidin-3(4H)-yl)pyridin-3-yl)-3-(trifluoromethyl)benzamide (I-3);

4-(4,4-dimethyl-4,5-dihydrooxazol-2-yl)-N-(6-methyl-5-(1-methyl-2-oxo-7-(phenylamino)-1,2-dihydropyrimido[4,5-d]pyrimidin-3(4H)-yl)pyridin-3-yl)benzamide (I-4);

3-(4,4-dimethyl-4,5-dihydrooxazol-2-yl)-N-(6-methyl-5-(1-methyl-2-oxo-7-(phenylamino)-1,2-dihydropyrimido[4,5-d]pyrimidin-3(4H)-yl)pyridin-3-yl)benzamide (I-5);

3-(t-butyl)-N-(6-methoxy-5-(1-methyl-2-oxo-7-(phenylamino)-1,2-dihydropyrimido[4,5-d]pyrimidin-3(4H)-yl)pyridin-3-yl)benzamide (I-6);

3-(4,4-dimethyl-4,5-dihydrooxazol-2-yl)-N-(6-methoxy-5-(1-methyl-2-oxo-7-(phenylamino)-1,2-dihydropyrimido[4,5-d]pyrimidin-3(4H)-yl)pyridin-3-yl)benzamide (I-7);

N-(6-chloro-5-(1-methyl-2-oxo-7-(phenylamino)-1,2-dihydropyrimido[4,5-d]pyrimidin-3(4H)-yl)pyridin-3-yl)-3-(trifluoromethyl)benzamide (I-8);

3-(t-butyl)-N-(6-chloro-5-(1-methyl-2-oxo-7-(phenylamino)-1,2-dihydropyrimido[4,5-d]pyrimidin-3(4H)-yl)pyridin-3-yl)benzamide (I-9);

2-(t-butyl)-N-(6-chloro-5-(1-methyl-2-oxo-7-(phenylamino)-1,2-dihydropyrimido[4,5-d]pyrimidin-3(4H)-yl)pyridin-3-yl)thiazole-4-carboxamide (I-10); and N-(6-chloro-5-(7-((4-hydroxyphenyl)amino)-1-methyl-2-oxo-1,2-dihydropyrimido[4,5-d]pyrimidin-3(4H)-yl)pyridin-3-yl)-3-(trifluoromethyl)benzamide (I-11), or pharmaceutically acceptable salt thereof.

* * * * *